(12) United States Patent
Chen et al.

(10) Patent No.: US 9,675,609 B2
(45) Date of Patent: Jun. 13, 2017

(54) NANO- AND MICRO-SIZED PARTICLES OF 20-CAMPTOTHECIN OR DERIVATIVE THEREOF AND PHARMACEUTICAL COMPOSITIONS CONTAINING SAME, AND TREATMENT OF CANCERS THEREWITH

(71) Applicant: Cao Pharmaceuticals Inc., Friendswood, TX (US)

(72) Inventors: Wenhao Chen, Queenstown (SG); Jiyao Zhang, Queenstown (SG); Zhisong Cao, Friendswood, TX (US)

(73) Assignee: Cao Pharmaceuticals Inc., Friendswood, TX (US)

( * ) Notice: Subject to any disclaimer, the term of this patent is extended or adjusted under 35 U.S.C. 154(b) by 0 days.

(21) Appl. No.: 14/938,057

(22) Filed: Nov. 11, 2015

(65) Prior Publication Data
US 2017/0128438 A1    May 11, 2017

(51) Int. Cl.
*C08J 3/075*    (2006.01)
*A61K 31/4745*    (2006.01)
(Continued)

(52) U.S. Cl.
CPC ........ *A61K 31/4745* (2013.01); *A61K 9/0053* (2013.01); *A61K 9/14* (2013.01);
(Continued)

(58) Field of Classification Search
CPC ................... C08J 3/075; A61K 47/36
See application file for complete search history.

(56) References Cited

U.S. PATENT DOCUMENTS

| | | | |
|---|---|---|---|
| 7,572,803 B2 * | 8/2009 | Cao | C07D 491/22 514/283 |
| 2004/0009229 A1 | 1/2004 | Unger et al. | |

(Continued)

OTHER PUBLICATIONS

Derakhshandeh et al, "Encapsulation of 9-nitrocamptothecin, a novel anticancer drug in biodegradable nanoparticles: Factorial design, characterization and release kinetics", European Journal of Pharmaceutics and Biopharmaceutics 66 (2007) 34-41.*

(Continued)

*Primary Examiner* — Carlos Azpuru
(74) *Attorney, Agent, or Firm* — Kilyk & Bowersox, P.L.L.C.

(57) ABSTRACT

A pharmaceutical composition is provided having particles of a physical mixture that contain at least one 20-camptothecin or a derivative thereof, at least one surfactant, at least one stabilizer, and at least one diluent. The particles have a mean particle size of less than about 2500 nm. The pharmaceutical composition can be nano- or micro-sized particles containing the 20-camptothecin esters or derivatives thereof as part of a physical mixture, which can provide the active compound in a water-soluble/dispersible, bioavailable form. The particles can be used as an oral pharmaceutical composition which comprises the nano- or micro-sized form of 20-camptothecin esters or derivatives, such as in an oral suspension (e.g., an aqueous suspension), or capsules, or caplets. The pharmaceutical composition can be used in the treatment of a cancer or malignant tumor in a patient by oral administration thereof in a therapeutically effective amount.

26 Claims, 11 Drawing Sheets

(51) Int. Cl.
| | |
|---|---|
| *A61K 9/14* | (2006.01) |
| *A61K 47/34* | (2017.01) |
| *A61K 47/38* | (2006.01) |
| *A61K 47/26* | (2006.01) |
| *A61K 9/00* | (2006.01) |
| *A61K 9/48* | (2006.01) |
| *A61K 47/36* | (2006.01) |

(52) U.S. Cl.
CPC ............ *A61K 9/4808* (2013.01); *A61K 47/26* (2013.01); *A61K 47/34* (2013.01); *A61K 47/36* (2013.01); *A61K 47/38* (2013.01); *C08J 3/075* (2013.01)

(56) References Cited

U.S. PATENT DOCUMENTS

| | | |
|---|---|---|
| 2008/0135245 A1 | 6/2008 | Smith et al. |
| 2009/0111845 A1 | 4/2009 | Cao |
| 2014/0314864 A1 | 10/2014 | Cheng et al. |
| 2015/0297521 A1 | 10/2015 | To et al. |

OTHER PUBLICATIONS

International Search Report and Written Opinion issued in corresponding International Patent Application No. PCT/US2016/060203 dated Jan. 10, 2017 (14 pages).

\* cited by examiner

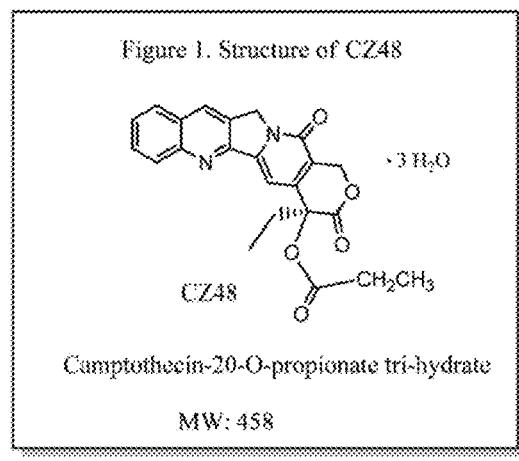
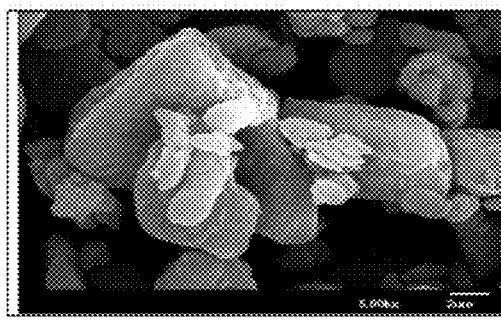
FIG. 2A
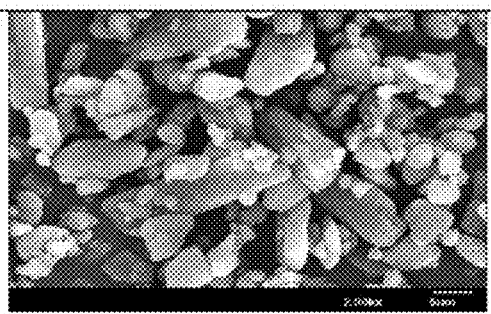
FIG. 2B

FIG. 7A
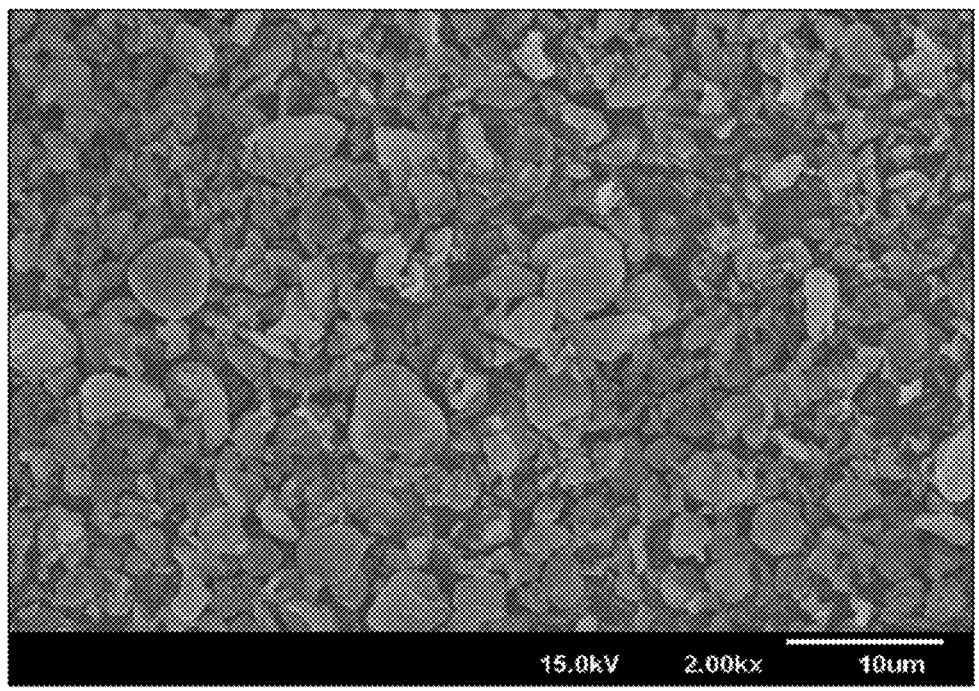
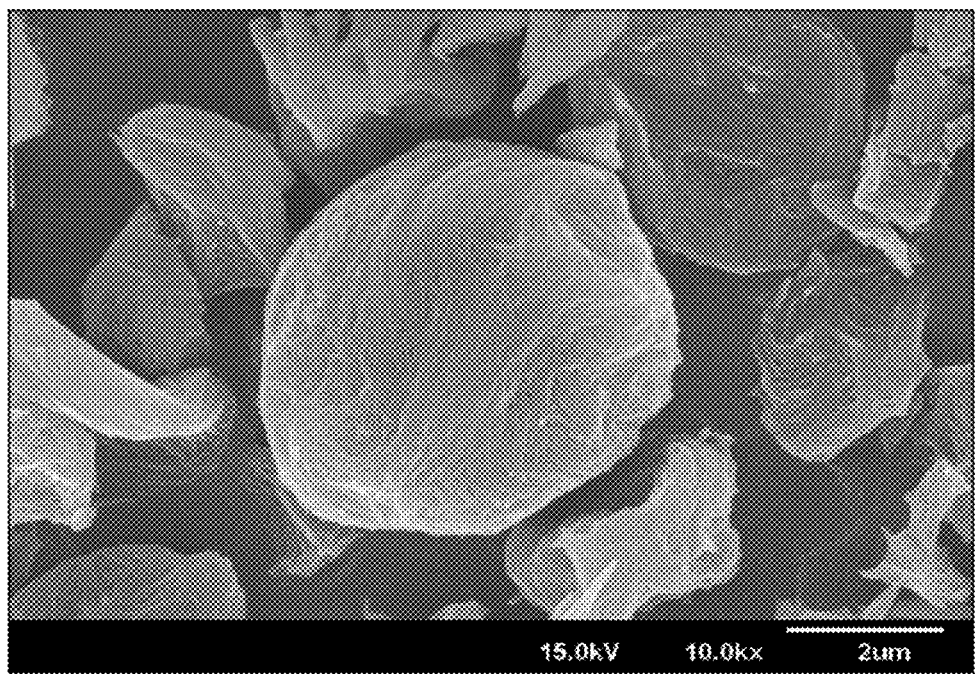
FIG. 7B

NANO- AND MICRO-SIZED PARTICLES OF 20-CAMPTOTHECIN OR DERIVATIVE THEREOF AND PHARMACEUTICAL COMPOSITIONS CONTAINING SAME, AND TREATMENT OF CANCERS THEREWITH

FIELD OF THE INVENTION

The present invention relates to nano- and micro-sized particles of 20-comptothecin and derivatives thereof for pharmaceutical compositions, and use of these particles and compositions containing them for treating cancer, malignant tumors, and the like.

BACKGROUND OF THE INVENTION

It is still a great challenge for cancer researchers and clinical oncologists to find better agents with a wider therapeutic index for treatment and with less restricted forms of administration.

Camptothecin, for instance, a cytotoxic alkaloid first isolated from the wood and bark of Camptotheca Acuminata (Nyssaceae) by Wall and his coworkers (J. Am. Chem. Soc. 88, 3888, 1966), was shown to have antitumor activity against the mouse leukemia L 1210 system. The structure of camptothecin, an alkaloid which has a commonly occurring indole alkaloid group (Heckendorf et al., J Org. Chem. 41, 2045, 1976), is shown below as Formula (X).

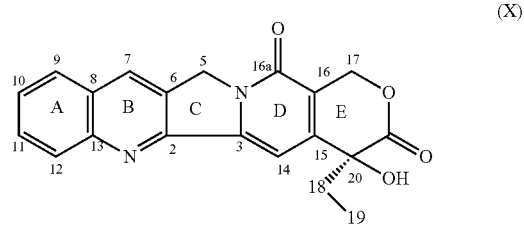

(X)

This compound ("CPT") has a pentacyclic ring system with only one asymmetrical center in ring E with a 20(S)-configuration. The pentacyclic ring system includes a pyrrolo [3, 4-b] quinoline moiety (rings A, B and C), a conjugated pyridone (ring D), and a six-membered lactone (ring E) with an α-hydroxyl group. Camptothecin was of great interest from the time of its initial isolation due to its noteworthy activity in the mouse leukemia L 1210 system. Earlier data for the antitumor activity of camptothecin were obtained by employing experimentally transplanted malignancies such as leukemia L 1210 in mice, or Walker 256 tumor in rats (Chem. Rev. 23, 385, 1973, Cancer Treat. Rep. 60, 1007, 1967). Subsequent clinical studies showed that this compound was not usable as an anticancer agent in vivo due to its high toxicity. Camptothecin itself is insoluble in water. Therefore, camptothecin was evaluated clinically as a water-soluble sodium carboxylate salt in the early times. This form of camptothecin produced severe toxicity and seemed devoid of anticancer activity (Gottlieb et al., Cancer Chemother. Rep. 54, 461, 1970, and 56, 103, 1972, Muggia et al., Cancer Chemother. Rep. 56, 515, 1972, Moertel et al., Cancer Chemother. Rep. 56, 95, 1972, and Schaeppi et al., Cancer Chemother. Rep. 5:25, 1974). These results caused the discontinuation of phase II trials. Continued evaluation of this agent showed that the sodium carboxylate salt is only 10% as potent as the native camptothecin with the closed lactone ring intact (Wall et al., In International Symposium on Biochemistry And Physiology of The Alkaloids, Mothes et al., eds., Academie—Verlag, Berlin, 77, 1969, Giovanella et al., Cancer res. 51, 3052, 1991). In addition, important parameters for antitumor activity in the camptothecin family have been established (Wall et al., Ann. Rev., Pharmacol. Toxicol. 17, 117, 1977). These results indicate that an intact lactone ring E and α-hydroxyl group are essential for antitumor activity.

In the middle 1980s it was found that the molecular target of camptothecins was the novel nuclear enzyme topoisomerase I. Hsiang Y H, Liu L F. Identification of mammalian DNA topoisomerase I as an intracellular target of anticancer drug camptothecin. Cancer Res 1988, 48, 1722. At approximately the same time, several new water-soluble camptothecin derivatives, including two compounds (topotecan and irinotecan) discussed earlier, were prepared and biologically evaluated. The subsequent clinical evaluations of the two compounds demonstrated the predictable toxicities and meaningful anticancer activity. Takimoto C H, Arbuck S G. Topoisomerase I targeting agents: the camptothecins. In: Chabner B A, Longo D L, eds., Cancer therapy & biotherapy: principles and practice, 3rd ed. Philadelphia: Lippincott Williams & Wilkins 2001, 579. Topotecan was approved in 1996 as second-line treatment for advanced ovarian cancer, and it later gained the indication for treating patients with refractory small cell lung cancer. At exactly the same time, irinotecan was registered for treating 5-florouracil-refractory advanced colorectal cancer. This actually represented the first new agent to gain approval for treating this disease in the United States in nearly 40 years.

In 1989, Giovanella et al. found that some of the non-water soluble derivatives of camptothecin have high antitumor activity against xenografts of human tumors (Giovanella et al., Science, 246, 1046, 1989). It was also shown that administration of camptothecin with closed lactone ring is superior to injections of water-soluble carboxylate salt (Giovanella et al., Cancer Res., 51, 3052, 1991). These findings further confirmed the importance of the intact lactone ring to biological activity.

Ring opening of 20(S)-camptothecin leads to much more potent anticancer activity in mice than in humans. In effect, CPT administered intramuscularly ("i.m."), subcutaneously ("s.c."), and intrastomach ("i.s.") has proven to be a very potent anticancer agent against human tumors in mice, i.e., when growing as xenotransplants in nude mice (Giovanella et al., Cancer Res. 51:3052, 1991). However, when tumors were treated with CPT in humans, a lower degree of anticancer activity in humans, than in mice, was exhibited (Stehlin et al., In Camptothecins: New Anticancer Agents, 1995, CRC Press, pp. 59-65). The same phenomenon was observed with other CPT-derivatives. In mice, 9-nitrocamptothecin ("9NC") has proven to be 2-3 times more potent than CPT against human tumor xenografts causing the total eradication of all the human malignancies treated (Pantazis et al., Cancer Res. 53:1577, 1993; Pantazis et al., Int. J. Cancer 53:863, 1995).

Ring opening is particularly problematic in that camptothecins exist in two distinct forms. The naturally-occurring camptothecin has an S-configuration and is 10 to 100 times more biologically active than the R-isomer. The S-configured lactone form is thought to be required for anti-tumor activity, and the carboxylate form usually relates to clinical toxicities. The molecule exists in equilibrium in aqueous solution. This equilibrium is pH-dependent. At physiological pH, i.e., 7 or above, the equilibrium equation is shown as follows:

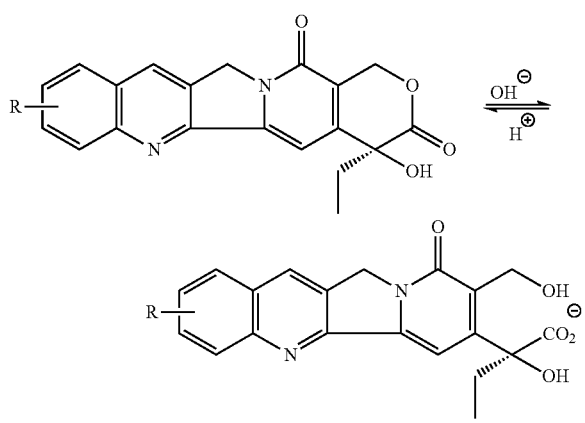

The hydrolysis reaction of the biological active lactone ring of camptothecins with water at higher pH gives the biologically inactive open form. Additionally, the hydrolysis problem with CPT and its analogs is exacerbated in human blood because the predominant human serum albumin (HSA) preferentially binds to the carboxylate form, which shifts the lactone/carboxylate equilibrium toward the inactive form (*J. Biochem.*, 212, 285-287, 1993; *Biochemistry*, 33, 10325-10336, 1994; *Biochemistry*, 33, 12540-12545, 1994). Accordingly, preserving the lactone ring of the molecule for a sufficient time for the tumor cells to cycle through the S-phase is a major challenge and has been the focus of a considerable amount of research.

A number of attempts have been made to provide derivatives of camptothecin having greater biological activity and enhanced stability. Many of these compounds are the products of modifications on the A, B, and C rings of the molecule, but few of these modifications have enhanced the stability of the lactone ring under physiological conditions. Other approaches have been more successful. For instance, acylating of 20-OH group provides a useful tool for the protection of lactone ring E. Wall et al., U.S. Pat. No. 4,943,579, describes several acylated camptothecin compounds having water solubility, although the lactone may not remain intact under physiological conditions. U.S. Pat. No. 5,968,943 to Cao et al. discloses CPT-derivatives which are effective antitumor agents.

Crystalline camptothecin-20-O-propinate hydrate is a semisynthetic compound derived from natural camptothecin, which usually is in powder form. The chemical structure of the compound is shown in FIG. 1. Due to insolubility in water or other aqueous metrics, these powders have been dispersed in lipids for administration. U.S. Pat. No. 7,572,803 B2, for instance, shows inter alia an example wherein this hydrated crystalline drug is finely suspended in cottonseed oil for oral administration to mice bearing human tumors.

While 20-camptothecin ester compounds exist that have been directly used in pharmaceutical compositions, there is a need for further compositions of 20-camptothecin esters which can deliver the active compounds in bioavailable form even though the starting compound itself is a water poor-soluble drug.

SUMMARY OF THE INVENTION

A feature of the present invention is a pharmaceutical composition which comprises nano- or micro-sized particles containing 20-camptothecin esters or derivatives thereof, which can provide the active compound in a water-soluble/dispersible, bioavailable form.

A further feature of the present invention is a pharmaceutical composition which comprises nano- or micro-sized particles that contain the 20-camptothecin esters or derivatives thereof in the form of a particulated physical mixture of the active ingredient and excipients.

Another feature of the present invention is an oral pharmaceutical composition which comprises the nano- or micro-sized particles of 20-camptothecin esters or derivatives and excipients.

A further feature of the present invention is an oral pharmaceutical composition which comprises the nano- or micro-sized particles of 20-camptothecin esters or derivatives and excipients in an oral suspension (e.g., an aqueous suspension), or capsules, or caplets.

Another feature of the present invention is a treatment of a cancer or malignant tumor in a patient comprising orally administering a therapeutically effective amount of the pharmaceutical composition comprising the nano- or micro-sized particles of 20-camptothecin esters or derivatives and excipients.

To achieve these and other advantages and in accordance with the purposes of the present invention, as embodied and broadly described herein, the present invention relates, in part, to a pharmaceutical composition comprising particles which are a physical mixture comprising at least one 20-camptothecin ester or a derivative thereof, at least one surfactant, at least one stabilizer, and at least one diluent, and the particles have a mean particle size of less than about 2500 nm.

The present invention further relates to oral administration forms of the pharmaceutical composition and treatment of a cancer or malignant tumor in a patient comprising orally administering a therapeutically effective amount of the pharmaceutical composition.

It is to be understood that both the foregoing general description and the following detailed description are exemplary and explanatory only and are intended to provide a further explanation of the present invention, as claimed.

The accompanying figures, which are incorporated in and constitute a part of this application, illustrate various features of the present invention and, together with the description, serve to explain the principles of the present invention. The features depicted in the figures are not necessarily drawn to scale. Similarly numbered elements in different figures represent similar components unless indicated otherwise.

BRIEF DESCRIPTION OF THE DRAWINGS

FIG. 1 shows a chemical structure of camptothecin-20-O-propionate hydrate (CZ48).

FIG. 2A shows an SEM image (5000×) of raw or native CZ48 powders.

FIG. 2B shows an SEM image (2000×) of the raw or native CZ48 powders.

FIG. 7A shows an SEM image (2000×) of CZ48 composite particles according to an example of the present application.

FIG. 7B shows an SEM image (10,000×) of CZ48 composite particles according to an example of the present application.

DETAILED DESCRIPTION OF THE INVENTION

Figure 3:
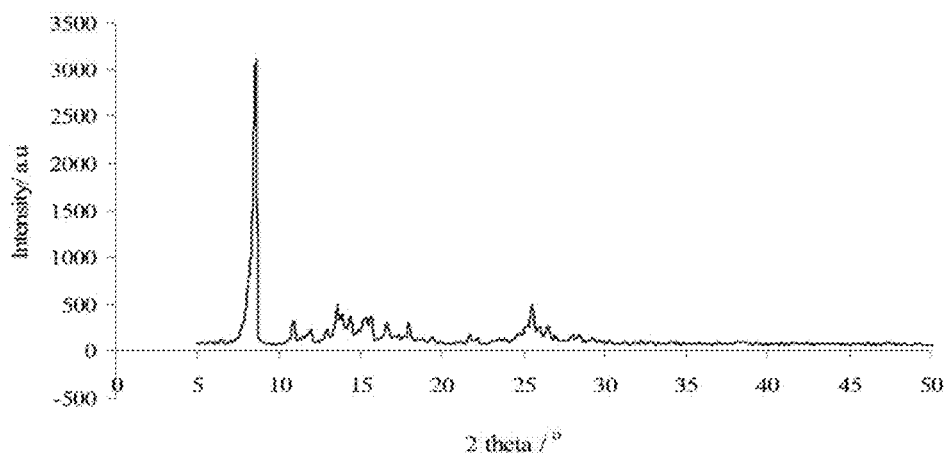
FIG. 3 shows an X-ray diffractometer (XRD) graph for the raw or native CZ48 powders.

A pharmaceutical composition is provided that can increase the bioavailability of 20-camptothecin or derivatives thereof as an active pharmaceutical ingredient or drug in a human body or animals. Nano- or micro-sized composite particles derived from a 20-camptothecin or derivative thereof (e.g., raw or native CZ48 powders), and other excipients such as indicated herein, are provided in the present application that are found to show increased bioavailability with respect to the drug ingredient thereof. The increased bioavailability can be obtained where the particles and compositions containing them are orally administered, and even though the starting compound itself is a water poor-soluble drug. The enhanced bioavailability can be provided with suspension of the particles in aqueous carriers or other oral delivery formats that do not require lipid carriers. Bioavailability (f) can refer to the systemically available fraction of the drug. The particles of the present application can deliver significant anti-cancer activity. As shown in examples herein, for instance, anti-cancer activity can be provided at much lower dosage levels of the active pharmaceutical ingredient (API), e.g., 20-camptothecin or derivative thereof, where administered via the particles of the present application in compositions as compared to administration of raw or native forms of the indicated API, such as CZ48 powders, in otherwise similar compositions and administration routes. As shown in examples herein, the particles of the present application demonstrate therapeutically significant anti-tumor activity against human tumor xenografts in animal models, and in comparison to the original CZ48 powders. Tumor size, for example, can be controlled by treatment with particles of the present application. Tumor control can refer to obtaining a reduced tumor size relative to the original tumor size at the onset of treatment, or a reduced size relative to that obtained by treatment with a control at similar conditions and time periods, or both. A "pharmaceutical composition" can refer to a mixture of the 20-camptothecin or derivative compounds or pharmaceutically acceptable salts thereof described herein, with other chemical components, such as excipients, and/or pharmaceutically acceptable carriers. The purpose of a pharmaceutical composition can be to facilitate administration of a compound or composite particle containing the compound to an organism.

The particles of the present application can be formed as a physical mixture in particle form containing raw 20-camptothecin or a derivative thereof compound and excipients including at least one surfactant, at least one stabilizer, and at least one diluent. The particles of the present application which comprise the physical mixture can be structurally integral discrete particles can be characterized as composite particles. In dry or dried form, the particles of the present application can be in a flowable powder form.

As shown in examples herein, the particles of the present application can have very different structures, properties and therapeutic performances from the raw (native or original) CZ48 powders. Particle size distribution (PSD) measurements described in the examples herein show that the particles of the present application can have a mean particle size that is much smaller than the original CZ48 particles. The composite particles of the present application can be, for example, about five (5) times smaller, or about four (4) times smaller, or about three times smaller, or about two times smaller, or other smaller values, than the original CZ48 particles. The particles of the present application can be more easily absorbed by human and animals than the starting CZ48 powders. The particles of the present application formed of a physical mixture of the drug compound and other excipients can have a mean particle size, for example, of from about 2500 nm or less, or from about 2000 nm or less, or from about 1800 nm or less, and an overall particle size distribution of from about 1 nm to about 3000 nm, or from about 50 nm to about 2750 nm, or from about 100 nm to about 2500 nm, or other nano- or micro-sized values and distributions such as indicated elsewhere herein. As shown in examples herein, the particles of the present application can be spherically shaped or substantially spherically shaped and morphologically different from raw CZ48 powders, which are rod or irregular rock shaped types of crystals. As shown in examples herein, the main peak of a X-ray diffractometer (XRD) spectrum of particles of the present application can be slightly left-shifted, compared to the original CZ48 powders. DSC measurements in the examples herein show that the melting point of particles of the present application can be about 80° C. lower than the original CZ48 powders.

A pharmaceutical composition of the present application can comprise the indicated particles as a physical mixture which comprises at least one 20-camptothecin or a derivative thereof, at least one surfactant, at least one stabilizer, and at least one diluent, and the particles have a mean particle size of about 2500 nm or less.

As shown by results of pre-clinical studies using animal models described herein, for example, particles of the present application can be therapeutically effective in treating cancers and tumors in human tumor xenografts planted in animal models, whereas aqueous suspensions of raw or native CZ48 powders have extremely low bioavailability and cannot reach a maximum tolerated dose (MTD). As shown in examples herein, a PK study conducted with the particles of the present application showed the API absorption in mice increased more than three fold. For example, the PK (pharmacokinetic) absorption of the active pharmaceutical agent (API) or drug component (e.g., 20-camptothecin or derivative thereof) from the composite particles of the present application in animal (mice and dog) models can be at least 150% higher (≥1.5× higher) or at least about 200% higher (≥2× higher), or at least 300% higher (≥3× higher), or at least 400% higher (≥4× higher), or at least 500% higher (≥5× higher), or other increases, than that of the raw CZ48 powders (e.g., based on Area Under Curve (AUC)) as the integral of the concentration-time curve). These increases can be based on where the composite particles of present application and raw CZ48 powders are administered in equivalent API dosages and administration routes, and "X" refers to the value for the raw CZ48 powders. As shown by examples herein, comparatively significantly higher pharmacological and therapeutic performance and effectiveness can be obtained with administration of CZ48 composite particles of the present application as compared to raw CZ48 powders. As shown in examples herein, the potency of the particles of the present application against human xenografts grown in nude mice also significantly increased when compared to the raw or native CZ48 powders. The particles of present application as tested against several human xenografts grown in nude mice have been found to have good anticancer activity with minimal toxicity in the animal models as seen from the animal survival rate in each experiment. As shown in examples herein, the particles of the present application show higher potency against human xenografts in nude mice than the raw or native CZ48 powders. For example, the particles of the present application show good activity against colon tumors at about ⅓ the dosage needed with the raw CZ48 powders to achieve the same result. As shown in the examples of the present application, the active pharmaceutical ingredient (API) or drug component of the particles of the present application has biodistributions in cancerous animal models which well encompasses tumor tissues relative to major organ tissues. These performance improvements obtained with composite particles of the present application are significant and surprising.

The term "nano-sized" herein can refer to a mean particle size of less than about 1000 nm, such as, for example, between about 50 nm to about 1000 nm. The term "nanoparticle" can refer to a particle with a particle size in the nano-sized range. The term "micro-sized" can refer to a mean particle size of between about 1 μm to about 1000 μm (between about 1000 nm to about 1 mm), such as, for example, between about 1000 μm and 3000 μm. The particle sizes may refer to the actual diameter of the particles where they are completely spherical or an equivalent diameter of substantially spherical particles. For particles that may be non-spherical, the particle size range can refer to the equivalent diameter of the particles relative to spherical particles or may refer to a dimension (length, breadth, height or thickness) of a non-spherical particle. The term "water poor-soluble drug" and the like can refer to a drug which is insoluble or poorly soluble in an aqueous medium, such as water. The solubility of a water poor-soluble drug can be, for example, about 0.1 mg/ml or less, or less than about 0.05 mg/ml, in an aqueous medium at physiological temperature and pH.

Particles of the present application can have more easily absorbable small scale size and high sphericity. The particles can be provided in narrow particle size distributions, which may assist processing and therapies involving the particles. As indicated, the small scale size of the particles can be nano-sizes, micro-sizes, or encompass both. The mean particle size of the particles of the present application can be in a range, for example, of about 2500 nm or less, or about 2000 nm or less, or about 1800 nm or less, or about 1500 nm or less, or about 1000 nm or less, or from about 50 nm to about 2500 nm, or from about 100 nm to about 2500 nm, or from 100 nm to about 2000 nm, or from about 250 nm to about 2000 nm, or from about 500 nm to about 2000 nm, or from about 100 nm to about 1800 nm, or from about 250 nm to about 1800 nm, or from about 500 nm to about 1800 nm, or other values.

The overall particle size distribution of the particles of the present application can be in a range, for example, of from about 1 nm to about 3000 nm, or from about 50 nm to about 3000 nm, or from about 100 nm to about 3000, or from about 50 nm to about 2750 nm, or from about 100 nm to about 2750 nm, or from about 50 nm to about 2500 nm, or from about 100 nm to about 2500 nm, or from 250 nm to about 2500 nm, or from about 500 nm to about 2500 nm, or from about 50 nm to about 2000 nm, or from about 100 nm to about 2000 nm, or from about 500 nm to about 2000 nm, or other values. At least 99 vol. %, or at least 90 vol. %, or at least 80 vol. %, or at least 70 vol. %, or at least 50 vol. %, of the particles can have a particle size of about 2500 nm or less, or about 2250 nm or less, or about 2000 nm or less, or about 1500 nm or less, or about 1000 nm or less, or other values.

The particles of the present application can be spherical, nearly spherical, or other shapes. For instance, the particles can be spherical and have a Krumbein sphericity of at least about 0.5, at least 0.6 or at least 0.7, at least 0.8, or at least 0.9, and/or a roundness of at least 0.4, at least 0.5, at least 0.6, at least 0.7, or at least 0.9. The term "spherical" can refer to roundness and sphericity on the Krumbein and Sloss Chart by visually grading 10 to 20 randomly selected particles. The particle shapes may be characterized, for example, using microscopic image analysis, such as using scanning electron microscopy (SEM). Spherical shapes, such as shapes having a Krumbein sphericity of at least 0.5 and/or roundness of at least 0.4, may be present in the particles in predominant amounts or other amounts. Spherical shapes, such as shapes having a Krumbein sphericity of at least 0.5 and/or roundness of at least 0.4, may be present in the particles in amounts, for example, of at least 50%, or at least 60%, or at least 75%, or at least 90%, or at least 95%, or at least 99%, or from 50 to 100%, or from 60 to 99%, or from 70 to 95%, or from 75 to 90%, or other values, based on total weight of the particles. Other particle shapes that are non-spherical may be present in the particles, such as rod, plate, or flake, needle. Non-spherical shapes, such as shapes having a Krumbein sphericity of less than 0.5 and/or roundness of less than 0.4, may be present in the particles in minor amounts or other amounts. Non-spherical shapes, such as shapes having a Krumbein sphericity of less than 0.5 and/or roundness of less than 0.4, may be present in the particles in amounts, for example, of less than 50 wt %, or less than 40 wt %, or less than 25 wt %, or less than 10 wt %, or less than 5 wt %, or less than 1 wt %, or from 0 to 49 wt %, or from 1 to 40 wt %, or from 5 to 30 wt %, or from 10 to 25 wt %, or other values, based on total weight of the particles.

The particles can be powder forms, such as dry flowable forms. The powders can be suspendable or dispersable in aqueous carriers, non-aqueous carriers, or both. The active pharmaceutical ingredient (e.g., 20-camptothecin or derivative), and the excipients used in forming a physical mixture therewith, such as the surfactant, the stabilizer, and the diluent, each can be in solid form in the particles. An "excipient" can refer to an inert substance added to a pharmaceutical composition to further facilitate administration of a compound. Additional excipients may be added to the physical mixture used in forming the particles, which may include, for example, absorption enhancers, different filling agents, binding agents, lubricants, sweeteners, flavoring agents, preservatives, diluents, disintegrants, effervescent agents, or others, in any combinations thereof.

The 20-camptothecin or derivative ingredient of the particles of the present application can be in a crystal form, or may be in a semi-crystalline form, or may be in an amorphous form. The term "crystalline" can refer to a material that contains a specific compound, which may be hydrated and/or solvated, and has sufficient crystal content to exhibit a discernible diffraction pattern by XRPD or other diffraction techniques. Often, a crystalline material that is obtained from a solvent by direct crystallization of a compound dissolved in a solution or interconversion of crystals obtained under different crystallization conditions, will have crystals that contain the solvent, termed a crystalline solvate. Examples of crystal properties include orientation of the chemical moieties of the compound with respect to each other within the crystal and predominance of a specific form of the compound, which is favored by the presence of an acid in the solvent composition. The 20-camptothecin or derivative compounds of the compositions of the present application can have a purity of from about 90% to about 100% by AUC (area under curve). The 20-camptothecin or derivative compounds of the compositions of the present application can have a purity, for example, of from about 95% to about 100% by AUC, or can have a purity of from about 99% to about 100% by AUC, such as from 99.3% to 99.999%; 99.5% to 99.999%; 99.75% to 99.999%; 99.85% to 99.999%, all by AUC, or other values. The 20-camptothecin or derivative compounds can have a melting point, for example, of from about 240° C. to about 243° C., such as 242° C. or about 242° C., or other values. This melting point(s) is especially preferred for the crystalline ester hydrate where $R_2$ is —$CH_2CH_3$. The melting points of the compounds of the present invention can be lower or higher than the above range when $R_2$ is a $CH_3$ or $C_3H_7$ or $C_4H_9$ or $C_6H_{13}$ group. Crystalline aliphatic ester hydrates of CPT having an S-configuration, an R-configuration, and/or racemic mixtures of both S- and R-isomers. The crystalline aliphatic ester hydrates of CPT derived from the natural camptothecin has only an S-configuration or primarily an S-configuration, such as 90% or higher, 95% or higher, 98% or higher, 99% or higher, or 99% to 99.99%.

A 20-camptothecin or derivative thereof which can be used in particles and compositions of the present application can be, for example, a camptothecin-20-ester or a 20-acyl-camptothecin. A 20-camptothecin or derivative thereof which can be used in particles and compositions of the present application can be, for example, at least one crystalline aliphatic ester of CPT in hydrated form having the formula:

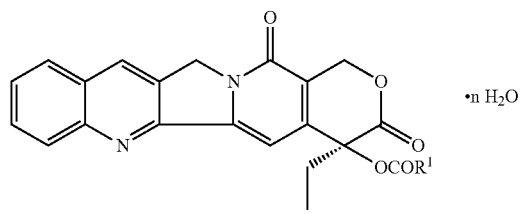

In this formula, n can represent any number ranging from 1 to 10 (e.g., 1, 2, 3, 4, 5, 6, 7, 8, 9, or 10). $R^1$ can represent a $C_2$-$C_6$ alkyl group (e.g., $C_2$, $C_3$, $C_4$, $C_5$, or $C_6$ alkyl), such as a $C_2$-$C_4$ alkyl group. In one or more embodiments, $R^1$ is —$CH_2CH_3$; —$CH_2CH_2CH_3$; —$CH_2CH_2CH_2CH_3$; or —$CH_2CH_2CH_2CH_2CH_2CH_3$. As one more specific embodiment, n represents 3 and $R^1$ is —$CH_2CH_3$ or —$CH_2CH_2CH_3$.

A pharmaceutical composition of the present application can comprise a 20-camptothecin or derivative thereof, for example, which is at least one camptothecin ester having the formula:

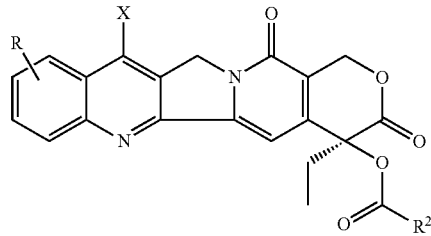

In this formula, the R group represents substituents on one of the rings of the structure above. In particular, R represents H, $NO_2$, $NH_2$, $N_3$, —OH, a halogen (e.g., F, Cl, Br, I), carboxyl (COOH), a $C_{1-16}$ alkyl group, $C_{2-16}$ alkenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_n NR_2^7$ (where $R^7$ can be H, or a $C_{1-8}$ alkyl group, n can be an integer of from 1 to about 8), hydroxyl, SH, $SR^8$ (where $R^8$ can be a $C_{1-8}$ alkyl group, an unsubstituted phenyl group, or a substituted phenyl group), a carbonyl group, (e.g., $COR^9$, where $R^9$ can be a $C_{1-8}$ alkyl group, an unsubstituted phenyl group, or a substituted phenyl group), a $SiR_3^{10}$ (where $R^{10}$ can be a $C_{1-4}$ alkyl group). The R group can be respectively positioned at the 9, or 10, or 11, or 12 position of ring A. R can also be a disubstituted 10, 11-O—$(CH_2)_y$—O-group (where y can be an integer of from 1 to 3). R can also be $C_{2-12}$ alkenyl group(s), $CF_3$(s), $CCl_3$(s), $CH_2F$(s), $CH_2Cl$(s), $CHF_2$(s), $CHCl_2$(s), OH(s), $OR^{12}$(s) (where $R^{12}$ can be a $C_{1-8}$ alkyl group, or a $C_{2-8}$ alkenyl group, or an aromatic group), $NR_2^{13}$(s) (where $R^{13}$ can be H, or $C_{1-4}$ alkyl group). X represents H, a $C_{1-8}$ alkyl group, a $C_{2-8}$ alkenyl group, a $C_{1-8}$ alkoxyl group, an aroxyl group, a $SiR_3^{11}$ group (where $R^{11}$ can be a $C_{1-4}$ alkyl group), or $CH_2NZY$ where Z and Y can be, independently, H, $C_{1-4}$ alkyl, or a $C_{1-4}$ halogenated alkyl group. Preferably R can be a hydrogen, halogen, halogen containing group, an alkyl group (e.g., $C_1$-$C_{15}$ alkyl group), —$NO_2$, —OH, alkoxy, or —$NH_2$. $R^2$ can be an alkyl group (such as $C_1$-$C_{15}$ alkyl), a cycloalkyl group (such as a $C_2$-$C_8$ cycloalkyl), an alkenyl group (such as $C_2$-$C_{15}$ alkenyl), or an epoxy group (such as $C_1$-$C_{15}$ epoxy group).

A 20-camptothecin or derivative thereof which can used in particles and compositions of the present application can be, for example, at least one camptothecin ester having the formula:

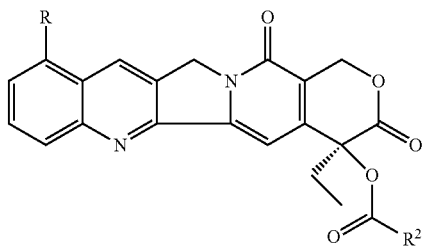

In this formula, R can be H or $NO_2$. $R^2$ represents $C_2$-$C_{15}$ alkyl group (such as a $C_2$-$C_4$ alkyl group or $C_6$-$C_{15}$ alkyl group), a $C_3$-$C_8$ cycloalkyl group, a $C_2$-$C_{15}$ alkenyl group or a $C_2$-$C_{15}$ epoxy group when R is H. When R is $NO_2$, $R^2$ is a $C_1$-$C_{15}$ alkyl group, a $C_3$-$C_8$ cycloalkyl group, a $C_2$-$C_{15}$ alkenyl group or a $C_2$-$C_{15}$ epoxy group. Preferably when R is H, $R^2$ is $CH_2CH_3$; $CH_2CH_2CH_3$; $CH_2CH_2CH_2CH_3$; $CH_2CH_2CH_2CH_2CH_2CH_3$; $CH_2CH_2CH_2CH_2CH_2CH_2CH_2CH_3$; or

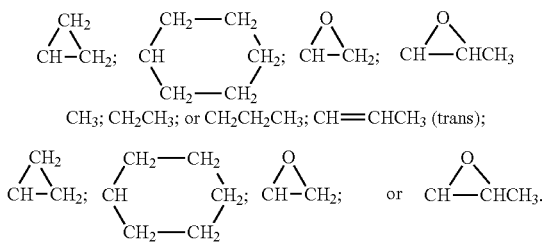

$CH_3$; $CH_2CH_3$; or $CH_2CH_2CH_3$; CH=$CHCH_3$ (trans);

The 20-camptothecin or derivative thereof can be camptothecin-20-O-propionate ("CZ48") hydrate. CZ48 powders can be obtained by using manufacturing methods such as disclosed in U.S. Pat. No. 7,572,803 B2, which is incorporated in its entirety by reference herein, or other methods.

The 20-camptothecin or derivative thereof may be a prodrug thereof. "Prodrugs" can refer to derivative compounds derivatized by the addition of a group that endows greater solubility to the compound desired to be delivered. Once in the body, the prodrug is typically acted upon by an enzyme, e.g., an esterase, amidase, or phosphatase, to generate the active compound.

The 20-camptothecin or derivative thereof can be included in a physical mixture used to form particles of the present application in amounts, for example, of from about 1 wt % to about 90 wt %, or from about 10 wt % to about 80 wt %, or from about 20 wt % to about 80 wt %., or from about 25 wt % to about 65 wt %, or from about 25 wt % to about 50 wt %, or from about 30 wt % to about 40 wt %, or other amounts, based on total weight of the physical mixture. These amounts can apply to the content of the 20-camptothecin or derivative thereof in the physical mixture as formulated and used to make the particles, and/or the content of the 20-camptothecin or derivative thereof in the finished particles as made from the physical mixture.

The surfactant(s) of the pharmaceutical composition of the present application may be a nonionic surfactant, anionic surfactant, cationic surfactant, or any combination thereof. The term "surfactant" can relate to any composition that is capable of altering surface tension between a liquid and any precipitated particles suspended in a liquid. A nonionic surfactant can be, for example, poloxamers, polyoxyethylene fatty alcohol ethers, sorbitan fatty acid esters, polyoxyethylene fatty acid esters, sorbitan esters, glycerol monostearates, cetyl alcohols; cetostearyl alcohols, stearyl alcohols, polaxamines, noncrystalline cellulose and synthetic phospholipids. Surfactants which are poloxamers can be, for example, a poly(ethylene oxide)-poly(propylene oxide)-poly(ethylene oxide) triblock copolymer wherein the poly(propylene oxide) block having an average molecular weight of from about 1500 to about 4500 Daltons and a poly(ethylene oxide) content of from about 50% to about 90% w/w of the copolymer. The surfactants can be commercially available ones. The poloxamer surfactants can be, for example, poloxamer members such as poloxamer P188 (PLURONIC F68), or poloxamer P237 (Pluronic F87, or poloxamer P338 (PLURONIC F108), or poloxamer P407 (or PLURONIC F127), or others. PLURONIC poloxamers are commercially available, for example, from BASF.

The surfactant can be included in the physical mixture used to form the pharmaceutical composition in amounts, for example, of from about 1 wt % to about 20 wt %, or from about 1 wt % to 15 wt %, or from about 1 wt % to about 10 wt %, or from about 2 wt % to about 8 wt %, or from about 2.5 wt % to about 5 wt %, or from about 3 wt % to about 4 wt %, or other amounts, based on total weight of the physical mixture. These amounts can apply to the content of the surfactant in the physical mixture as formulated and used to make the particles, and/or the surfactant content in the finished particles as made from the physical mixture.

The stabilizer of the pharmaceutical composition can be a cellulose, a cellulose derivative, or any combinations thereof. The "stabilizer" can refer to a material that when present in the pharmaceutical composition can reduce the occurrence of degradation of an API as compared to the same composition without the stabilizer. The stabilizer can be, for example, methylcellulose, ethyl cellulose, hydroxyethyl cellulose, hydroxypropyl cellulose, hydroxypropyl methylcellulose, sodium carboxymethyl cellulose, cellulose acetate, cellulose acetate butyrate, cellulose phthalate, cellulose acetate phthalate, hydroxypropylmethylcellulose phthalate, or any combinations thereof. The stabilizers can be commercially available ones, and the cellulose family can be used, and hydroxypropyl methyl cellulose E3 (HPMC E3) can be used.

The stabilizer can be included in the physical mixture used to form the pharmaceutical composition in amounts, for example, of from about 1 wt % to about 20 wt %, or from about 1 wt % to 15 wt %, or from about 1 wt % to about 10 wt %, or from about 2 wt % to about 8 wt %, or from about 2.5 wt % to about 5 wt %, or from about 3 wt % to about 4 wt %, or other amounts, based on total weight of the physical mixture. These amounts can apply to the content of the stabilizer in the physical mixture as formulated and used to make the particles, and/or the stabilizer content in the finished particles as made from the physical mixture.

The diluent of the pharmaceutical composition can be a sugar, starch, sugar alcohol, or any combinations thereof. A "diluent" of the pharmaceutical composition can refer to inactive ingredients that may be used, for example, as fillers, binders, disintegrants (e.g., assist a tablet to break apart in the digestive system), or flavor enhancers, or other functions. The diluent can be, for example, mannitol, xylitol, lactitol, sorbitol, lactose, maltitol, cellobitol, erythritol, isomalt, potato starch, corn starch, glucose, sucrose, dextran, or any combinations thereof. Commercially available sugars can be used as the diluents. For example, mannitol and lactose can be used, and specifically, mannitol can be used as the diluent in making the particles of the present application.

The diluent can be included in the physical mixture used to form the pharmaceutical composition in amounts, for example, of from about 5 wt % to about 95 wt %, or from about 10 wt % to about 90 wt %, or from about 20 wt % to about 85 wt %, or from about 30 wt % to about 80 wt %, or from about 40 wt % to about 80 wt %, or from about 50 wt % to about 70 wt %, or from about 55 wt % to about 65 wt %, or other amounts, based on total weight of the physical mixture. These amounts can apply to the content of the diluent in the physical mixture as formulated and used to make the particles, and/or the diluent content in the finished particles as made from the physical mixture.

The pharmaceutical composition of the present application can contain the active pharmaceutical ingredient (e.g., 20-camptothecin or derivative), surfactant, stabilizer, and diluent in any respective amounts wherein the physical mixture can be formed into discrete particles containing at least these components. The physical mixture can comprise, for example, from about 1 wt % to about 90 wt % 20-camptothecin or derivative, from about 1 wt % to about 20 wt % surfactant, from about 1 wt % to about 20 wt % stabilizer, and from about 5 wt % to about 95 wt % diluent, based on total weight of the mixture. The physical mixture can comprise from about 10 wt % to about 80 wt % 20-camptothecin or derivative, from about 1 wt % to about 10 wt % surfactant, from about 1 wt % to about 10 wt % stabilizer, and from about 10 wt % to about 90 wt % diluent, based on total weight of the mixture. The mixture can comprise from about 25 wt % to about 50 wt % 20-camptothecin or derivative, from about 1 wt % to about 10 wt % surfactant, from about 1 wt % to about 10 wt % stabilizer, and from about 40 wt % to about 80 wt % diluent, based on total weight of the mixture. The physical mixture can comprise from about 10 wt % to about 80 wt % camptothecin-20-O-propionate hydrate, from about 1 wt % to about 10 wt % surfactant, from about 1 wt % to about 10 wt % stabilizer, and from about 10 wt % to about 90 wt % diluent, based on total weight of the mixture. The mixture can comprise from about 25 wt % to about 50 wt % camptothecin-20-O-propionate hydrate, from about 1 wt % to about 10 wt % poloxamer surfactant, from about 1 wt % to about 10 wt % cellulose-based stabilizer, and from about 40 wt % to about 80 wt % sugar diluent, based on total weight of the mixture. These amounts of the active pharmaceutical ingredients and indicated excipients can apply to the content of them in the physical mixture as formulated and used to make the particles, and/or to their respective amounts in the finished particles.

A pharmaceutical composition of the present application can be useful for treating cancer in a warm-blooded animal. A pharmaceutical composition of the present application can be oral administered. The composition is prepared in accordance with known formulation techniques to provide a composition suitable for oral, topical, transdermal, rectal, by inhalation, parenteral (intravenous, intramuscular, or intraperitoneal) administration, and the like. Detailed guidance for preparing compositions of the invention is found by reference to the 18th or 19th Edition of Remington's Pharmaceutical. Sciences, Published by the Mack Publishing Co., Easton, Pa. 18040. The pertinent portions are incorporated herein by reference.

Unit doses or multiple dose forms are contemplated, each offering advantages in certain clinical settings. The unit dose would contain a predetermined quantity of active compound present in the particles calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved, and any limitations inherent in the art of preparing the particular compound for treatment of cancer. A unit dose can contain a therapeutically effective amount sufficient to treat cancer in a subject and may contain, for example, from about 1 to about 1000 mg of the active pharmaceutical ingredient (API) (e.g., 20-camptothecin or derivative thereof), based on the API's total content in the administered particles, or can be from about 25 to about 1000 mg of the API, or from about 50 to about 1000 mg of the API, or from about 100 to about 1000 mg of the API, or from about 250 mg to about 1000 mg of the API, or from about 50 to about 750 mg of the API, or from about 100 to about 750 mg of the API, or from about 250 to about 750 mg of the API, or from about 50 to about 500 mg of the API, or from about 100 to about 500 mg of the API, or from about 250 to about 500 mg of the API, or other amounts.

The pharmaceutical composition may be formulated for oral administration in liquid form, solid form, aerosol form, or other orally ingestible forms.

For oral liquid administration, a pharmaceutical suspension can comprise the pharmaceutical composition in carrier fluid. The carrier fluid can be aqueous, or non-aqueous. An aqueous carrier can be water (e.g., pure water, deionized water, ultrafiltered water, distilled water, etc.). The pharmaceutical composition can be suspended or dispersed in an aqueous carrier, such as water, with substantially uniform dispersion of the particles throughout the fluid without any problematic settling or clumping (aggregating). A pharmaceutical suspension can contain a unit dose of the 20-camptothecin or derivative, based on its total content in the particles suspended in the carrier, which can be from about 1 to about 1000 mg of the API, or from about 50 to about 1000 mg of the API, or from about 50 to about 500 mg of the API, or from about 100 to about 500 mg of the API, or other amounts.

Aqueous suspensions can contain the particles alone or in admixture with excipients suitable for the manufacture of aqueous suspensions. Such excipients can be suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water can provide the particles including the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid. The particles and pharmaceutical compositions used in the methods herein may be in the form of an oil-in-water emulsion.

The pharmaceutical compositions can be administered as ingestible capsules or caplets. The pharmaceutical composition can be incorporated as a loose dry powder form into a capsule. The pharmaceutical composition can be encapsulated within a relatively stable shell or capsule using known capsule materials, methods and equipment, allowing the composition to be taken orally. Hard-shelled capsules may be used, for example, for dry, powdered forms of the pharmaceutical composition. Soft-shelled capsules may be used, for example, for forms of the pharmaceutical composition that are dissolved or suspended in oil. Both of these classes of capsules can be made, for example, from aqueous solutions of gelling agents. The gelling agents can be, for example, gelatin (e.g., animal protein), plant polysaccharides and their derivatives such as carrageenans and modified forms of starch and cellulose. Other ingredients which can be added to the gelling agent solution can be, for example, plasticizers such as glycerin and/or sorbitol to decrease the capsule's hardness, coloring agents, preservatives, distintegrants, lubricants and surface treatment, or others.

The pharmaceutical composition can be incorporated into a caplet comprising a tablet containing the pharmaceutical composition, wherein the tablet is coated with a protective coating. It is to be appreciated that the type of process used to form the tablets can include known methods to a person skilled in the art and may include a direct compression process or wet-granulation process, or other tablet preparing methods. The tablet preparing method may be, for example, rotary compression, compacting roller technology such as a chilsonator or drop roller, or by molding, casting or extrusion technologies. Protective coating materials and methods for coating them onto tablet cores to cover or enrobe them are known, which can be applied to forming a protective coating on the tablet. Such outer coatings can contain, for example, cellulose derivatives as major ingredients which can have relatively high melting points, e.g., greater than 135° C., or coatings that contain a thermoplastic material and have lower melting points, such as fats such as cocoa butter, hydrogenated vegetable oils such as palm kernel, cottonseed oil, sunflower oil, and soybean oil, mono, di, and triglycerides, phospholipids, waxes such as Carnauba wax, spermaceti wax, beeswax, candelilla wax, shellac wax, microcrystalline wax, and paraffin wax, water soluble polymers such as polyethylene glycol, polyethylene oxides, sucrose esters, or any combinations thereof. Other additives may be included in the protective coating, such as, for example, the types indicated above for the capsule formulations.

The capsules and caplets can contain a unit dose of the 20-camptothecin or derivative thereof, based on its total content in the particles that are encapsulated in the capsule or contained in the tablet, which can be from about 0.01 to about 2500 mg of the API, or from about 0.05 to about 1500 mg of the API, or from about 1 to about 1000 mg of the API, or from about 50 to about 1000 mg of the API, or from about 50 to about 500 mg of the API, or from about 100 to about 500 mg of the API, or other amounts.

A percentage or proportion of the API in particles that can be used in a final composition and preparations, such as oral pharmaceutical compositions, may be varied and may conveniently range between 1 and 99 wt % of the weight of the final form, e.g., aqueous suspension, tablet, caplet, or other amounts and final forms. The amount in such therapeutically useful compositions is such that a suitable dosage of the active pharmaceutical ingredient component of the particles can be provided. Pharmaceutical compositions according to the present application can be prepared, for example, such that an oral dosage unit form contains between about 1 to about 99% by weight, or from about 1 to about 90% by weight, or from about 5 to about 85% by weight, or from about 5 to about 75% by weight, or from about 5 to about 50% by weight, or from about 10 to about 80% by weight, or from about 10 to about 65% by weight, or from about 10 to about 50% by weight, of the powders, of the present application, or other amounts. The proportion of the API in the particles can be as indicated hereinabove.

A suitable composition (formulation) of an oral dosage unit may additionally contain other excipients and additives, such as binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like; artificial or natural sweeteners; preservatives; effervescent agents; or others, in any combinations.

Various other materials may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91-93 for a fuller discussion.

The particles and pharmaceutical compositions containing them of the present application can be used in methods to treat various forms of cancer, malignant tumors, and/or precursors of cancer or precursors of malignant tumors. The method can include treating a cancer or a malignant tumor in a patient by administering the compound or a composition containing the compound of the present invention. The method can include administering an effective amount of the compound or a composition containing the compound of the present invention to treat the cancer or malignant tumor, wherein the cancer or malignant tumor is responsive to the treatment using the compound or composition containing the compound of the present invention. As described further below, various cancers and malignant tumors can be treated. The particles and compositions containing them of the present application are effective in treating human or animal patients for cancers, malignant tumors, neoplasms, or cancer precursors. Specific examples include, but are not limited to, leukemia, melanoma, liver, breast, colorectal, rectal, ovary, prostate, stomach, bladder, desmoplastic small round cell tumor (DSRCT), pancreas, lung, kidney, colon, central nervous system tumors, or any combination thereof. As used herein, the term "malignant tumor" is intended to encompass all forms of human or animal carcinomas, sarcomas and melanomas which occur in the poorly differentiated, moderately differentiated, and well differentiated forms.

Another feature of the particles and compositions containing them of the present application relates to the relatively low or no apparent overall toxicity of the drugs administered in accordance herewith. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity. The particles containing the 20-camptocethin or derivative and compositions containing them of the present application can demonstrate a broad spectrum of activity with no observable toxicity in mice at variable dose ranges. The therapeutic index can be determined by testing in nude mice, such as the average therapeutic index from testing mice having a tumor xenograft that is a cancer tumor of bladder, breast, colon, kidney, lung, melanoma, pancreas, prostate, ovarian, and/or any of the cancers mentioned herein. Further, the therapeutic index of this form of the agent can be tremendously improved compared with other anticancer agents clinically used today by oncologists. The therapeutic index of the crystalline aliphatic ester hydrates of 20-CPT as administered in the particles and compositions containing them of the present application can range, for example, from 2 to 500 (e.g., 3 to 500, 4 to 50, 3 to 10, 4 to 15, 5 to 20, 8 to 20, 10 to 20, 25 to 500, 50 to 500, 75 to 500, 100 to 500, 150 to 500, 200 to 500, 250 to 500, 300 to 500, 350 to 500, 400 to 500, 450 to 500) when 2000 mg/kg is considered to be the most tolerated dose. The therapeutic index for most anti-cancer agents currently used in clinical oncology, however, is approximately 1, which is very narrow. Further, none of the anti-cancer agents currently used can be continuously used for a long duration at the effective dose. The particles and compositions containing them of the present application can be continuously used, for example, on a daily or weekly or monthly basis for 2 months, 3 months to 12 months, 4 months to 15 months, 5 months to 15 months, 6 months to 24 months, or more.

A pharmaceutical composition of the present application can be orally administered in a therapeutically effective amount to a subject in the need thereof. A "therapeutically effective amount" of active pharmaceutical agent can mean that particles of the present application contain an amount of the active pharmaceutical compound (API)(e.g., 20-camptothecin or derivative thereof), which will inhibit the growth of, or retard cancer, or kill malignant cells, and cause the regression and palliation of malignant tumors, i.e., reduce the volume or size of such tumors or eliminate the tumor entirely. The therapeutically effective amount can vary depending on factors known to those of skill in the art, such as the type of cell growth, the mode and regimen of administration, the size of the subject, the severity of the cell growth, etc. One of skill in the art would be able to consider such factors and make the determination regarding the effective amount. This can be achieved with the present invention. A "therapeutically effective antitumor therapy" can refer to a therapy which is effective to maintain or decrease the size, e.g., volume, of a primary tumor or metastatic tumor. This can be achieved with the particles and compositions of the present application.

The therapeutically effective amount of the active pharmaceutical compound (API)(e.g., 20-camptothecin or derivative thereof) in particles of the present application can be a daily dose, given as a single dose or in divided doses, containing a dosage level of from about 0.01 mg/kg to about 2500 mg/kg (in weight of API), or from about 0.1 mg/kg to about 2250 mg/kg, or from about 1 mg/kg to about 2000 mg/kg, or from about 5 mg/kg to about 1750 mg/kg, or from about 10 mg/kg to about 1500 mg/kg, or from about 25 mg/kg to about 1000 mg/kg, or from about 100 mg/kg to about 500 mg/kg, or about 50 mg/kg, or about 100 mg/kg, or about 400 mg/kg, or about 500 mg/kg, or about 1000 mg/kg, or about 2000 mg/kg of body weight. The dose contains at least one API, which may be a single chemical structural type of API, or a combination of different API's having different chemical structures relative to each other (e.g., a plurality of different API's, such as 2, 3, 4, 5, or more different API's).

With mammals, including humans, the effective amounts can be administered on the basis of body surface area. The interrelationship of dosages varies for animals of various sizes and species, and for humans (based on mg/M$^2$ of body surface) is described by E. J. Freireich et al., Cancer Chemother. Rep., 50(4):219 (1966). Body surface area may be approximately determined from the height and weight of an individual (see, e.g., Scientific Tables, Geigy Pharmaceuticals, Ardsley, N.Y. pp. 537-538 (1970)). An effective amount of the camptothecin compounds in the present invention for treatment of mammals, including humans, can range, for example, from about 10 to about 3500 mg/m$^2$ of body surface per day, or from about 25 to about 2500 mg/m$^2$ of body surface per day, or from about 50 to about 1500 mg/m$^2$ of body surface per day, or from about 100 to about 1000 mg/m$^2$ of body surface per day, or from about 100 to about 750 mg/m$^2$ of body surface per day, or other amounts.

The methods and compositions of the present application may also be used in conjunction with other well known therapeutic agents that are selected for their particular usefulness against the condition that is being treated. For example, the instant compounds may be useful in combination with known anti-cancer and cytotoxic agents. Further, the methods and compositions may also be useful in combination with other inhibitors of parts of the signaling pathway that links cell surface growth factor receptors to nuclear signals initiating cellular proliferation.

Nano-sized or micro-sized composite particles of the present application can be formed of the physical mixtures containing the 20-camptothecin or derivative and the other indicated excipients by any suitable techniques. High gravity controlled precipitation (HGCP), for example, can be used to make the composite particles of the present application.

High gravity controlled precipitation (HGCP) technology is a technology designed specifically for the preparation of micro- or nano-sized particles by controlled precipitation. It utilizes high gravity forces to intensify mass transfer between phases. During the process, fluids are mixed under high shear created by the high gravity using a rotating packed bed to achieve micro-mixing in a precipitant solution. The term "precipitant solution" can refer to a solution which comprises one or more solutes dissolved in a solvent (S) or a mixture of solvents that, when added to an anti-solvent (AS), causes a precipitate to form. The term "anti-solvent" can refer to a solvent or a mixture of solvents which, when added in a sufficient quantity to the precipitant solution, cause the solute to precipitate from the precipitant solution without removal or reduction of the solvent medium. The anti-solvent used may be substantially miscible with the solvent of the precipitant solution such that the interaction between the anti-solvent and the solvent allows the solute to precipitate from the precipitant solution.

In a method of making particles of the present application, for example, the precipitant solution can contain the active pharmaceutical ingredient. The active pharmaceutical ingredient can be dissolved in a solvent(s), e.g., an organic solvent(s), to obtain a drug solution. Excipients, e.g., surfactant, stabilizer, and diluent as indicated herein, can be dissolved in water or other solution to obtain an excipient solution as an anti-solvent solution. The precipitant solution and anti-solvent (excipient) solution can be mixed together under the high gravity controlled precipitation to generate a suspension, such as a nano-suspension. This process can provide all particles with the same growth time. As a result, the particles prepared by HGCP can possess smaller size, narrower size distribution, or both. A nano-sized and/or micro-sized mixed suspension of particles can be obtained by HGCP, which can be dried to remove solvent therefrom. The suspension obtained by HGCP can be immediately dried, such as by spray-drying, to form composite particles of the present application. Removal of the solvent can cause excipients present to solidify and thereby can form nano-sized and/or micro-sized composite particles. Each nano-sized or micro-sized particle can be comprised of the drug (API) particles dispersed in a solid matrix of the excipients, such as the surfactant, stabilizer, and diluent.

Methods and equipment which can be adapted to make particles of the present application by HGCP can be those disclosed, for example, in U.S. Patent Application No. 2011/0306539 A1, which is incorporated in its entirety by reference herein.

The HGCP process may comprise the step of impinging the mixture of precipitant solution and anti-solvent solution substantially throughout the mixing zone to induce the impingement force. The mixing zone can be located within an enclosed chamber of a molecular mixing unit. The molecular mixing unit may further comprise at least two fluid inlets to introduce fluids such as the precipitant solution and the anti-solvent solution into the enclosed chamber and optionally one outlet to allow suspended particles to be removed from the enclosed chamber. The molecular mixing unit may comprise an agitator within the enclosed chamber. The agitating step to induce the shear force during the reacting step may be provided by an agitator and shear means as previously disclosed in the International Patent Application number. PCT/SG2007/000333 (published as WO 2008/041951), the disclosure of which is herein incorporated as reference. The use of an agitator to impart high shear force to the mixing fluids in the mixing zone may ensure that the precipitant solution and the anti-solvent fluid may be adequately and homogeneously mixed in a short period of time, such as less than about 1 hour, less than about 1 minute, less than about 10 s, less than about 1 s, or less than about 10 ms, to form an intimate mixture leading to formation of a precipitate of drug particles. The operating temperature and pressure of the molecular mixing unit are not particularly limited but in most embodiments, the operating temperature may be in the range of about 0° C. to about 100° C. while the operating pressure may be at atmospheric pressure. The operating temperature may be in the range of about 20° C. to about 90° C., or may be less than about 40° C., or may be selected based on the boiling point of the solvent used in the precipitant solution, the boiling point of the anti-solvent as well as the stability of the drug or excipient used in the process. The agitator in the molecular mixing unit can comprise a rotator-stator (or rotor-stator) disposed within an enclosed chamber, the rotator (or rotor) being rotatable about a longitudinal axis and the stator being stationary for imparting a high shear force to the mixture of precipitant solution and anti-solvent solution within the mixing zone. The agitator can comprise a packed bed disposed within the enclosed chamber, the packed bed being rotatable about a longitudinal axis for imparting a shear force to the mixture of precipitant solution and anti-solvent solution within the mixing zone in use. The packed bed may aid to split the precipitant solution and the anti-solvent solution into thin films, threads and very fine droplets under the high shear environment. The packing may have a surface area in the range of about 100-3000 $m^2/m^3$. The packing can be such that it is structured packing or random packing. The packing can be a packing of the wire mesh type packing that can be made from a relatively inert material such as stainless steel, plain metal alloy, titanium metal or plastic. The packing can be substantially cylindrically-shaped and comprises at least one mesh layer. The packing may be comprised of a plurality of overlapping mesh layers.

Applying a shear force to the mixture of precipitant solution and anti-solvent solution within the mixing zone may be undertaken by a shear means. The shear means can be in the form of a rolling mesh to form a cylindrical shear means, wherein the cylindrical section has sides formed by a plurality of overlapping mesh layers. The mesh may have a mesh size of about 0.05 mm to about 3 mm or about 0.1 mm to about 0.5 mm: The mesh may have mesh porosity of at least 90%, or more than 95%. The packed bed can be mounted on a shaft in the mixing zone and rotates in the mixing zone. As the packed bed rotates, the packing imparts high shear onto the injected precipitant solution and, anti-solvent solution. The rotating packed bed can be cylindrically shaped and defines a hollow to accommodate the inlets for the precipitant solution and anti-solvent solution.

The molecular mixing unit may comprise at least one liquid outlet means for draining the suspension of particles from the mixing zone when the mixing unit is operated in either batch mode or continuous mode. The suspension may be drained directly into the inlet of a drying unit. This allows for the possibility of an integrated unit made up of the micro-mixing unit and the drying unit. This may allow for the possibility of scaling up to larger capacities and hence increases the yield of drug particles obtained. When directly feeding the suspension from the molecular mixing unit into the drying unit, a continuous process may be created such that the precipitated particles may not be substantially subjected to an ageing step. Accordingly, the time interval between the formation of the precipitate drug particles and introduction of the particles into the drying unit may be in the order of seconds or milliseconds. Due to the lack of, or at least, minimal ageing time of the formed particles, the particles may be prevented from growing in size such that the stability of the drug particles may be controlled.

The drying unit may be a spray dryer. Suitable spray-drying techniques are described, for example, by K. Masters in "Spray Drying Handbook", John Wiley & Sons, New York, 1984. Generally, during spray-drying, heat from a hot gas such as heated air or nitrogen is used to evaporate the solution in which the particles obtained by HGCP are suspended. The particles, while suspended in the mixture, can be atomized by an atomizer to form an atomized droplet wherein the liquid of the atomized droplet is rapidly evaporated by application of heat. Due to the small nature of the atomized droplet, and the application of heat, the liquid medium is rapidly evaporated. A rotary atomizer can be used. Examples of spray driers using rotary atomization include Niro spray drier Mobile Minor.

By rapidly spray drying the suspension, solid particles can be obtained that contain the active pharmaceutical agent or drug compound distributed and physically retained within a solid matrix comprising the excipients. Accordingly, the API may be dispersed uniformly or non-uniformly in the dried particles.

The physical properties of the spray-dried particles can depend on a number of parameters, such as direction of flow of the drying gas in the drying chamber; the degree and uniformity of atomization due to the type of atomizer used; the amount of drug particles in the liquid medium in % solids concentration; the temperature of the liquid medium; efficiency of the collection mechanism and choice of anti-solvent used. The flow of the drying gas in the drying chamber may be substantially opposite to the flow of the atomized solution (that is, countercurrent flow) or the flow of the drying gas in the drying chamber may be in the same direction as the flow of the atomized solution (that is, cocurrent flow). Some spray dryers may combine both countercurrent and cocurrent flow in the drying chamber. The type of flow pattern in the drying chamber may aid in the generation of turbulence in the drying chamber and hence, may lead to an increased rate of interaction between the drying gas and the atomized droplets in order to increase the rate of heat transfer from the drying gas to the atomized droplets. Atomization of the suspension into droplets may be effected through atomizing devices such as rotary atomizers and nozzle atomizers. Exemplary nozzle atomizers include pressure nozzles and two-fluid nozzles. The types of atomizers used may determine the size of the atomized droplets, the degree of atomization as well as the spray characteristics such as spray angle or spray direction of the droplets sprayed from the atomizers into the drying chamber. The inlet temperature of the drying gas into the spray dryer may be in a range from about 50° C. to about 220° C., or other temperatures. The outlet temperature may be dependent on the inlet temperature selected and may be, for example, in a range of about 20° C. to about 120° C., or other temperatures. The outlet temperature may be controlled in order to ensure that the activity of the API is retained. The drying time to convert a droplet to dry powder may be less than about 10 seconds, particularly less than about 5 seconds and more particularly about 1 second.

As an illustration of a method for manufacturing composite particles of the present application, for example, raw CZ48 powders (or other 20-camptothecin compounds or derivatives thereof) as API can be dissolved in a solvent or solvents to obtain a CZ48 precipitant solution. This CZ48 precipitant solution can be mixed with an anti-solvent containing surfactant(s), stabilizer(s), and diluent(s), using HGCP to generate a nano- or micronized CZ48 suspension. The suspension obtained by HGCP can be spray dried. The solvents can be, for example, acetone, ethanol, acetonitrile, N-methylpyrrolidone, methanol, pyridine, tetrahydrofuran, chloroform, dichloromethane, dimethylsulfone, N-dimethylformamide, or the combinations of these solvents. The anti-solvents can be, for example, petroleum ether and water, such as de-ionized (DI) water. DI water is preferred. Those solvents mixable with water, such as, ethanol, acetone, and acetonitrile can thus also be useful. Pyridine, methanol, and tetrahydrofuran, though mixable with water, may have less desirable profiles of toxicity than acetone, acetonitrile, and ethanol. For example, the combination of ethanol and acetonitrile in ratio of 1:3 to 3:1 (v/v), such as 1:1, can be used as the solvent and DI water can be used as the anti-solvent. The ratio range of solvent to anti-solvent (v/v) can be from 1:20 to 1:1. The 1:10 or 1:5 ratio (v/v) of acetonitrile/ethanol (1:1, v/v) to water is desirable. The surfactants, stabilizers and diluent used as excipients can be the materials indicated herein. The particle sizes of spray-dried CZ48 particles generated by this HGCP process with S/AS can range, for example, from 100 nm to 2500 nm. After the spray-drying, the CZ48 composite particles obtained can contain, for example, 10-80% CZ48 (API), 1-10% surfactants, 1-10% stabilizers, and 10-90% diluents (all in weights %), or other proportions.

The present invention includes the following aspects/embodiments/features in any order and/or in any combination:

1. A pharmaceutical composition comprising particles which are a physical mixture comprising at least one 20-camptothecin or a derivative thereof, at least one surfactant, at least one stabilizer, and at least one diluent, and the particles have a mean particle size of about 2500 nm or less.

2. The pharmaceutical composition of any preceding or following embodiment/feature/aspect, wherein the particles having a mean particle size of from about 1600 nm to about 2000 nm.

3. The pharmaceutical composition of any preceding or following embodiment/feature/aspect, wherein at least 90 vol. % of the particles have a particle size of about 2500 nm or less.

4. The pharmaceutical composition of any preceding or following embodiment/feature/aspect, wherein the composition is a powder.

5. The pharmaceutical composition of any preceding or following embodiment/feature/aspect, wherein the particles are discrete composite particles.

6. The pharmaceutical composition of any preceding or following embodiment/feature/aspect, wherein particles have at least one of a Krumbein sphericity of at least about 0.5 and a roundness of at least about 0.4.

7. The pharmaceutical composition of any preceding or following embodiment/feature/aspect, wherein the active pharmaceutical ingredient, the surfactant, the stabilizer, and the diluent each are in solid form.

8. The pharmaceutical composition of any preceding or following embodiment/feature/aspect, wherein the 20-camptothecin or derivative thereof is at least one crystalline aliphatic ester of CPT in hydrated form having the formula wherein n can represent any number ranging from 1 to 10, and $R^1$ represents a $C_2$-$C_6$ alkyl group.

9. The pharmaceutical composition of any preceding or following embodiment/feature/aspect, wherein the 20-camptothecin or derivative thereof is at least one camptothecin ester having the formula:

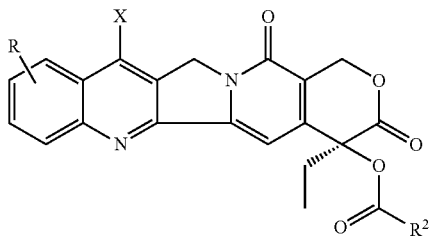

wherein R represents H, $NO_2$, $NH_2$, $N_3$, —OH, a halogen, carboxyl, a $C_{1-16}$ alkyl group, $C_{2-16}$ alkenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_nNR_2^7$ where $R^7$ can be H or a $C_{1-8}$ alkyl group and n can be an integer of from 1 to about 8, hydroxyl, SH, $SR^8$ where $R^8$ can be a $C_{1-8}$ alkyl group or an unsubstituted phenyl group or a substituted phenyl group, a carbonyl group $COR^9$ where $R^9$ can be a $C_{1-8}$ alkyl group or an unsubstituted phenyl group or a substituted phenyl group, or a $SiR_3^{10}$ where $R^{10}$ can be a $C_{1-4}$ alkyl group, and $R^2$ can be an alkyl group, a cycloalkyl group, an alkenyl group, or an epoxy group.

10. The pharmaceutical composition of any preceding or following embodiment/feature/aspect, wherein the 20-camptothecin or derivative thereof is camptothecin-20-O-propionate hydrate.

11. The pharmaceutical composition of any preceding or following embodiment/feature/aspect, wherein said surfactant is a poloxamer.

12. The pharmaceutical composition of any preceding or following embodiment/feature/aspect, wherein said surfactant is a poly(ethylene oxide)-poly(propylene oxide)-poly(ethylene oxide) triblock copolymer wherein the poly(propylene oxide) block having an average molecular weight of from about 1500 to about 4500 Daltons and a poly(ethylene oxide) content of from about 50% to about 90% w/w of the copolymer.

13. The pharmaceutical composition of any preceding or following embodiment/feature/aspect, wherein said stabilizer is at least one of a cellulose and a cellulose derivative.

14. The pharmaceutical composition of any preceding or following embodiment/feature/aspect, wherein said stabilizer is methylcellulose, ethyl cellulose, hydroxyethyl cellulose, hydroxypropyl cellulose, hydroxypropyl methylcellulose, sodium carboxymethyl cellulose, cellulose acetate, cellulose actetate butyrate, cellulose phthalate, cellulose acetate phthalate, hydroxypropylmethylcellulose phthalate, or any combinations thereof.

15. The pharmaceutical composition of any preceding or following embodiment/feature/aspect, wherein said diluent is mannitol, xylitol, lactitol, sorbitol, lactose, maltitol, cellobitol, erythritol, isomalt, potato starch, corn starch, glucose, sucrose, dextran, or any combinations thereof.

16. The pharmaceutical composition of any preceding or following embodiment/feature/aspect, wherein said diluent is a sugar.

17. The pharmaceutical composition of any preceding or following embodiment/feature/aspect, wherein said diluent is mannitol.

18. The pharmaceutical composition of any preceding or following embodiment/feature/aspect, wherein the mixture comprises from about 1 wt % to about 90 wt % 20-camptothecin or a derivative thereof, from about 1 wt % to about 20 wt % surfactant, from about 1 wt % to about 20 wt % stabilizer, and from about 5 wt % to about 95 wt % diluent, based on total weight of the mixture.

19. The pharmaceutical composition of any preceding or following embodiment/feature/aspect, wherein the mixture comprises from about 10 wt % to about 80 wt % camptothecin-20-O-propionate hydrate, from about 1 wt % to about 10 wt % surfactant, from about 1 wt % to about 10 wt % stabilizer, and from about 10 wt % to about 90 wt % diluent, based on total weight of the mixture.

20. The pharmaceutical composition of any preceding or following embodiment/feature/aspect, wherein the mixture comprises from about 25 wt % to about 50 wt % camptothecin-20-O-propionate hydrate, from about 1 wt % to about 10 wt % poloxamer surfactant, from about 1 wt % to about 10 wt % cellulose-based stabilizer, and from about 40 wt % to about 80 wt % sugar diluent, based on total weight of the mixture.

21. A pharmaceutical composition of any preceding or following embodiment/feature/aspect, wherein the composition is suitable for oral administration.

22. An oral pharmaceutical suspension comprising the pharmaceutical composition of any preceding or following embodiment/feature/aspect claim suspended in carrier fluid.

23. An oral pharmaceutical suspension comprising the pharmaceutical composition of any preceding or following embodiment/feature/aspect suspended in water.

24. A capsule containing the pharmaceutical composition of any preceding or following embodiment/feature/aspect.

25. A capsule containing the pharmaceutical composition of any preceding or following embodiment/feature/aspect in loose dry powder form.

26. A caplet comprising a tablet containing the pharmaceutical composition of any preceding or following embodiment/feature/aspect, wherein the tablet is coated with a protective coating.

27. Treatment of a cancer or malignant tumor in a patient comprising orally administering a therapeutically effective amount of the pharmaceutical composition of any preceding or following embodiment/feature/aspect.

28. The treatment according to any preceding or following embodiment/feature/aspect, wherein the 20-camptothecin or derivative thereof is at least one crystalline aliphatic ester of CPT in hydrated form having the formula

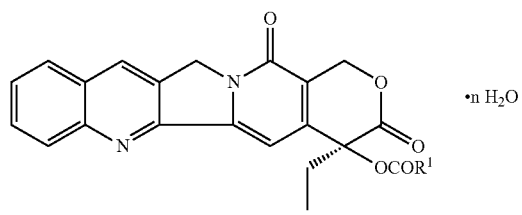

wherein n can represent any number ranging from 1 to 10, and $R^1$ represents a $C_2$-$C_6$ alkyl group.

29. The treatment according to any preceding or following embodiment/feature/aspect, wherein the 20-camptothecin or derivative thereof is at least one camptothecin ester having the formula:

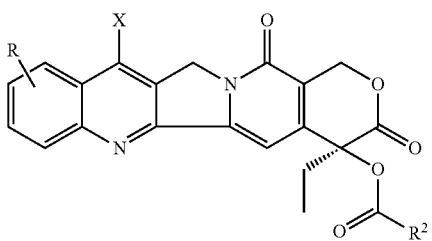

wherein R represents H, $NO_2$, $NH_2$, $N_3$, —OH, a halogen, carboxyl, a $C_{1-16}$ alkyl group, $C_{2-16}$ alkenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_n NR_2^7$ where $R^7$ can be H or a $C_{1-8}$ alkyl group and n can be an integer of from 1 to about 8, hydroxyl, SH, $SR^8$ where $R^8$ can be a $C_{1-8}$ alkyl group or an unsubstituted phenyl group or a substituted phenyl group, a carbonyl group $COR^9$ where $R^9$ can be a $C_{1-8}$ alkyl group or an unsubstituted phenyl group or a substituted phenyl group, or a $SiR_3^{10}$ where $R^{10}$ can be a $C_{1-4}$ alkyl group, and $R^2$ can be an alkyl group, a cycloalkyl group, an alkenyl group, or an epoxy group.

30. The treatment according to any preceding or following embodiment/feature/aspect, wherein the 20-camptothecin or derivative thereof is camptothecin-20-O-propionate hydrate.

31. The treatment according to any preceding or following embodiment/feature/aspect, wherein the therapeutically effective amount is a daily dose containing a dosage level of from about 0.01 mg/kg to about 2500 mg/kg of body weight of the at least one 20-camptothecin or a derivative thereof.

32. The treatment according to any preceding or following embodiment/feature/aspect, wherein the daily dose is administered in a single dose or divided doses.

33. The treatment according to any preceding or following embodiment/feature/aspect, wherein the 20-camptothecin or derivative thereof is camptothecin-20-O-propionate hydrate.

34. Treatment of a cancer or malignant tumor in a patient comprising orally administering a therapeutically effective amount of the oral pharmaceutical suspension of any preceding or following embodiment/feature/aspect.

35. Treatment of a cancer or malignant tumor in a patient comprising orally administering a therapeutically effective amount of the capsule of any preceding or following embodiment/feature/aspect.

36. Treatment of a cancer or malignant tumor in a patient comprising orally administering a therapeutically effective amount of the caplet of any preceding or following embodiment/feature/aspect.

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples, which are intended to be only exemplary of the present invention. Unless indicated otherwise, all amounts, percentages, ratios and the like used herein are by weight.

EXAMPLES

Comparative Example 1

Crystalline camptothecin-20-O-propinate hydrate (CZ48) having the chemical structure shown in FIG. 1 was charac-terized. The raw or native CZ48 was in the form of pale yellow powders of the compound. The characterization of raw CZ48 powders was done by various means including field emission scanning electron microscope (SEM), X-ray diffractometer (XRD), differential scanning colorimeter (DSC), and particle size distribution (PSD) pattern. The results are respectively shown in FIGS. 2A-B, 3, 4, and 5, which are further discussed herein.

Figure 4:
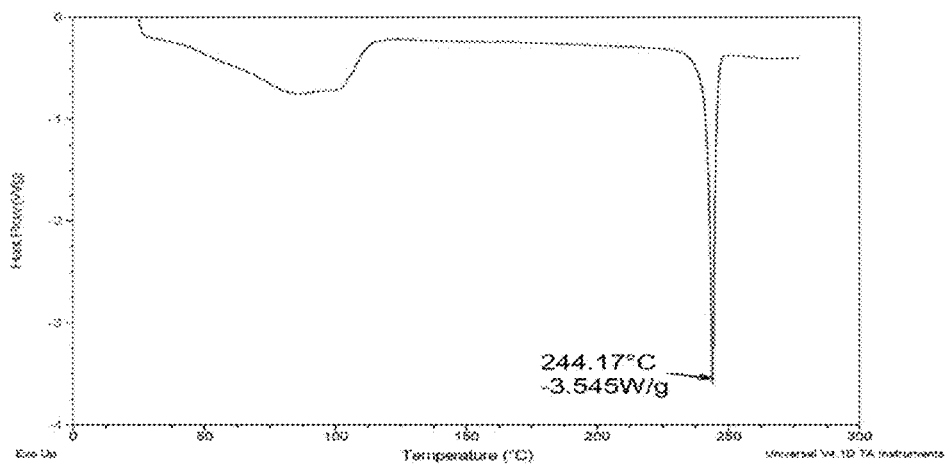
FIG. 4 shows a graph of differential scanning colorimeter (DSC) results for the raw or native CZ48 powders.
Figure 5:
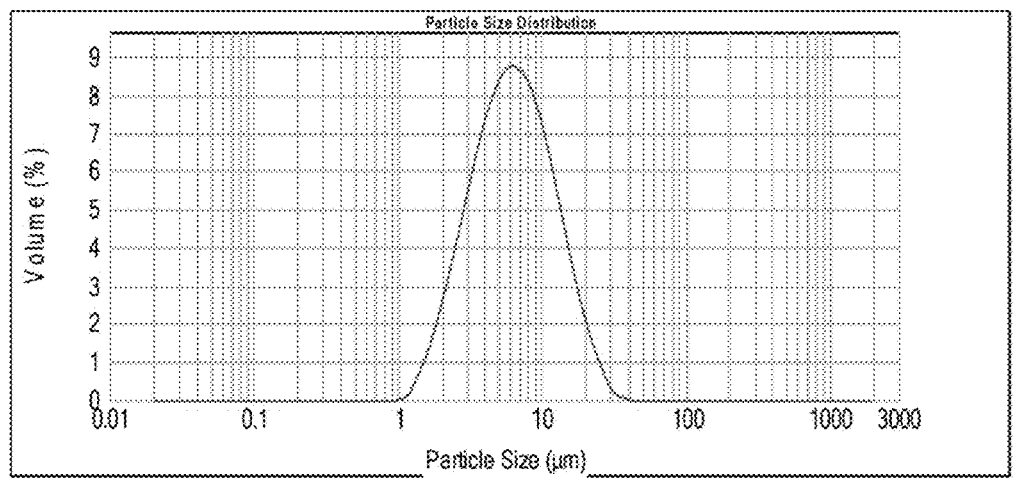
FIG. 5 shows a graph of particle size distribution (PSD) of the raw or native CZ48 powders.

As shown in the SEM images of the raw CZ48 powders in FIGS. 2A and 2B, the examined raw CZ48 powders are made of rod or irregular rock-shaped types of crystals. FIG. 3 shows an XRD pattern obtained of the CZ48 powders. FIG. 4 shows DSC results of the raw CZ48 powders. The particle size distribution (PSD) of raw CZ48 powders was analyzed and measured by a Malvern Laser Diffraction Analyzer, and the results are shown in FIG. 5 and Table 1.

TABLE 1

| PSD results of Raw CZ48 powders (μm). | | | |
|---|---|---|---|
| d(0.1) | d(0.5) | d(0.9) | D[4,3] |
| 2.612 | 6.220 | 14.556 | 7.612 |

Raw or native CZ48 powders have been intensively tested against human xenografts grown in nude mice. Due to insolubility in water or any other aqueous metrics, raw CZ48 powders are suspended in cottonseed oil when being used for treating nude mice carrying human xenografts. The suspension of raw CZ48 powders in cottonseed oil has been found effective against almost every type of 29 human xenografts tested thus far with only one prostate tumor responded negatively, achieving a 97% response rate (28 out of 29). This suspension is almost non-toxic in mice. A toxicity study with this suspension in healthy nude mice showed that animals did not lose any body weights, instead gained slightly, during 280 day's treatment with a high dose of this suspension (2000 mg/kg). It was also found during the biological evaluation that this form of formulation had a low bioavailability in mice (<10%). The pharmacokinetic (PK) studies were performed with multiple doses of 50, 100, 400, 500, 1000, and 2000 mg/kg and showed that the $C_{max}$s of the raw CZ48 drug were greater than 100 ng/ml when the dose was 100 mg/kg or higher. It was observed that this 100 ng/ml of $C_{max}$ was the minimum requirement for a positive effect in cancerous mice. $C_{max}$ refers to the peak plasma concentration of the drug after administration.

An investigational new drug (IND) application was approved by US Food and Drug Administration (FDA) for testing in human clinical trial because of the indicated pharmacodynamic effects in mice, using a suspension of raw CZ48 powders in pure water. Thus far, 40 patients with various cancers have been treated with the water suspension in phase 1 safety studies. The Maximum Tolerated Dose (MTD) is not reached yet. The dose has reached 6 grams per day. Compared to the oil suspension in mice, the suspension of raw CZ48 powders in pure water is less absorbed by patients. The PK determination of the blood samples from all patients enrolled thus far in phase 1 clinical trials showed that there was not a single patient having the $C_{max}$ reach the 100 ng/ml marks, implying that the bioavailability of the suspension of CZ48 powders in pure water is extremely low in a human body. Thus, the MTD has not reached in patients taking a daily dose of 6 grams of the powders.

Example 1

Experiments were conducted to investigate the bioavailability of particles made from physical mixtures of raw CZ48 powders and excipients comprising surfactant, stabilizer, and diluent. High Gravity Controlled Precipitation (HGCP) was used in combination with a spray drying (SD) process to obtain CZ48 composite particles.

Preparation of Composite CZ48 Particles

Pure native (raw) CZ48 powders (1.68 g) were dissolved in 100 ml acetonitrile/ethanol (1:1, v/v) to obtain the drug solution. Surfactant P338 (0.195 g), stabilizer HPMC E3 (0.195 g), and diluent mannitol (2.93 g) were dissolved in 1000 ml DI water to obtain the excipient solution. The native CZ48 powders were manufactured by methods disclosed in the above-indicated U.S. Pat. No. 7,572,803 B2. The drug and excipient solutions were mixed under the high gravity (high gravity controlled precipitation) to generate a CZ48 nano-suspension. The CZ48 nano-suspension was immediately spray-dried by a spray drier. After drying at 50° C. for 6 hours, 3.8 g of CZ48 composite particles were obtained with a mean particle size of 1799 nm. Using the S/AS ratio of 1:10 or 1:5 of ethanol/acetonitrile to DI water gave the CZ48 composite particles having the indicated mean size of 1799 nm. Recovery rate for this process was approximately 76%. The DSC measurement showed that the matrix particles had a major peak at 164° C. The content of the product powders measured by HPLC was 33.6% CZ48 (API), 3.9% P338 (F108), 3.9% HPMC E3, and 58.6% mannitol.

The product particles have the following characterizations as shown by FIGS. 6, 7A-B, 8, and 9, which are described in more detail herein.

Figure 6:
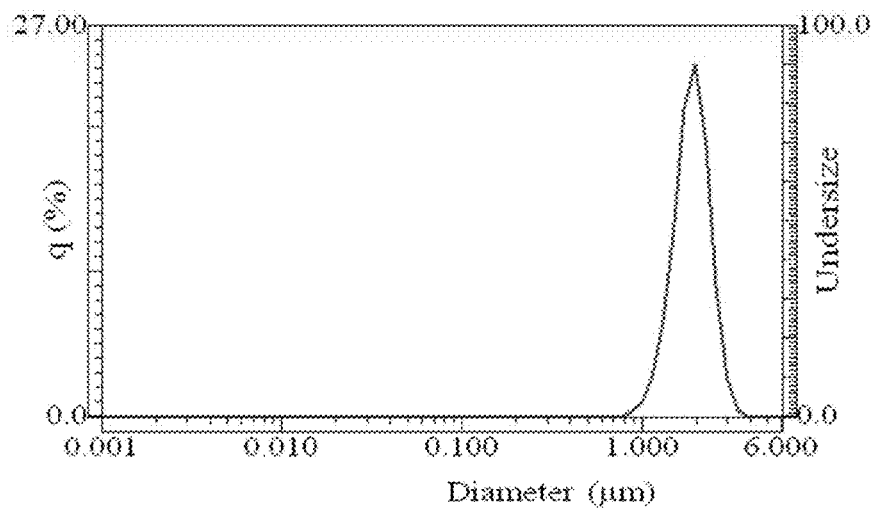
FIG. 6 shows a graph of PSD of re-dispersed CZ48 composite particles in water according to an example of the present application.

FIG. 6 shows the PSD pattern of the re-dispersed CZ48 composite particles in water. The particle size distribution (PSD) of the CZ48 composite particles was analyzed and measured by a Malvern Laser Diffraction Analyzer, and the results are shown in Table 2.

TABLE 2

PSD results of CZ48 composite powders (μm).

| D10 μm | D16 μm | D50 μm | D84 μm | D90 μm | mean μm |
|---|---|---|---|---|---|
| 1.3012 | 1.3923 | 1.7773 | 2.2041 | 2.3394 | 1.7999 |

The PSD measurement showed that the CZ48 composite particles had a mean particle size of 1799 nm, 4 times smaller than the original (raw) CZ48 particles.

FIGS. 7A-B shows SEM images of the CZ48 composite particles. The SEM images (FIGS. 7A-B) show that the particles of CZ48 are spherically shape and morphologically different from the raw CZ48 powders, which have rod-rock shapes as shown in FIGS. 2A-B.

Figure 8:
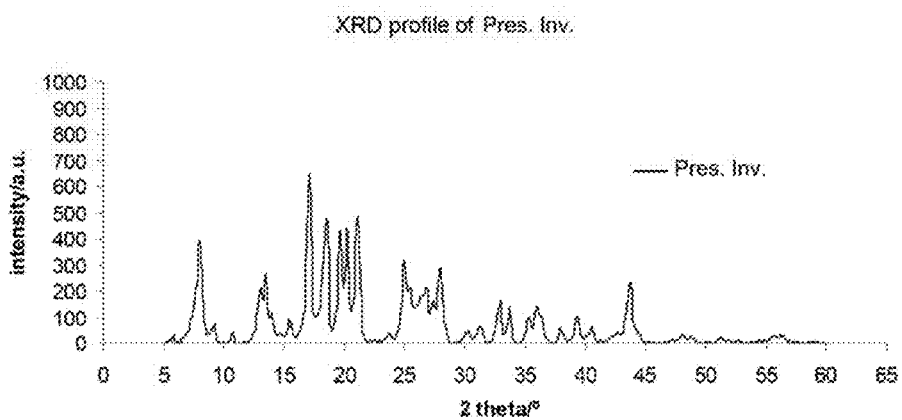
FIG. 8 shows an X-ray diffractometer (XRD) graph for CZ48 composite particles according to an example of the present application.
Figure 9:
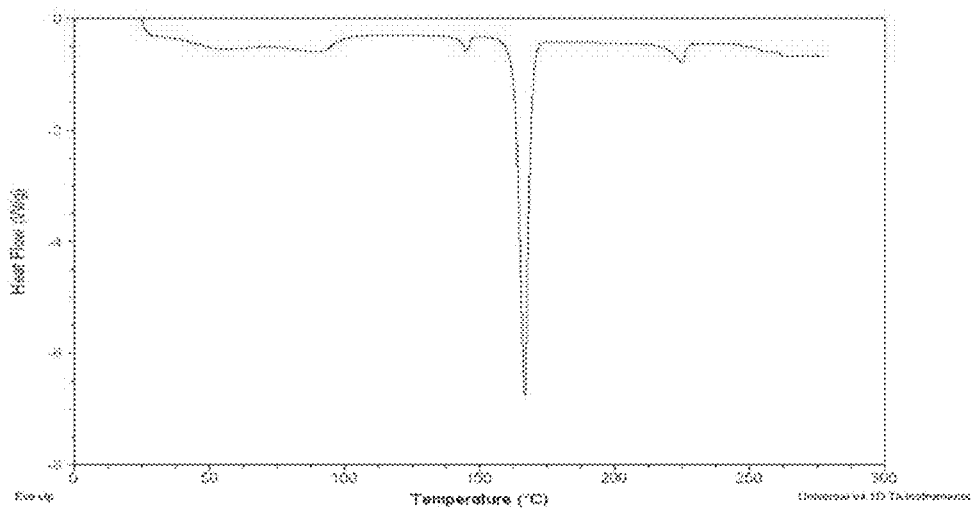
FIG. 9 shows a graph of differential scanning colorimeter (DSC) results for CZ48 composite particles according to an example of the present application.

FIG. 8 shows a XRD profile of the CZ48 composite particles. FIG. 9 shows a DSC profile of the CZ48 composite particles.

Figure 10:
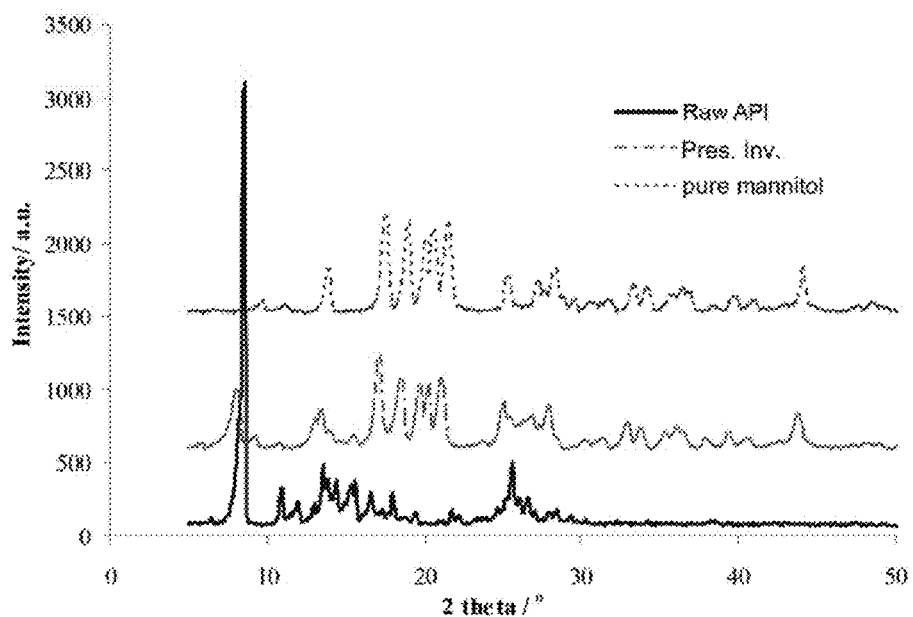
FIG. 10 shows a comparison of XRD patterns between the original materials of raw CZ48 particles and mannitol, and the CZ48 composite particles according to an example of the present application.
Figure 11:
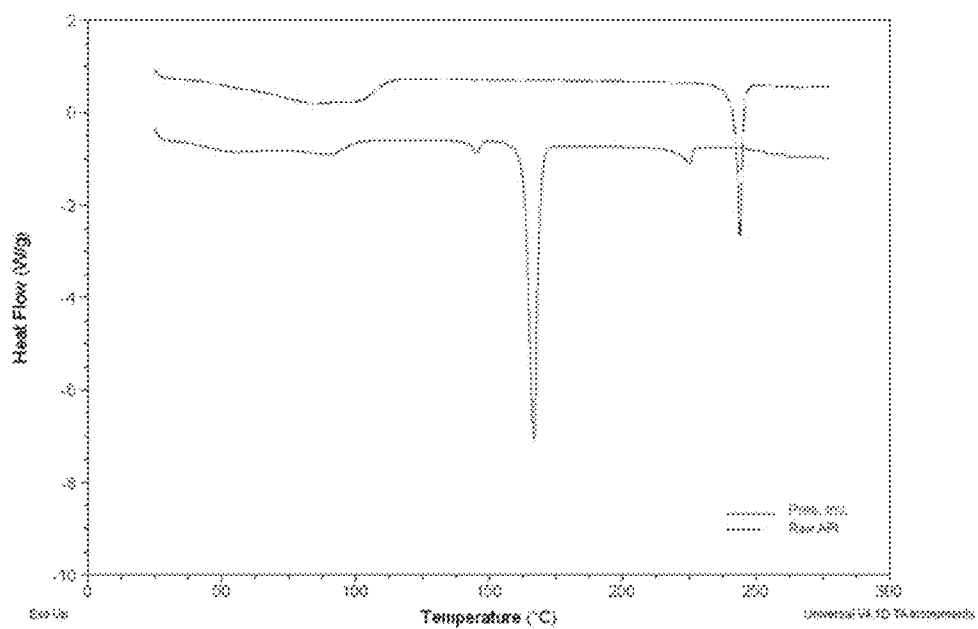
FIG. 11 shows a comparison of DSC patterns between the raw CZ48 particles and the CZ48 composite particles according to an example of the present application.

FIG. 10 shows a comparison of XRD patterns between the CZ48 composite particles and original materials (raw API and mannitol). As can be seen from FIG. 10, the main peak of the XRD spectrum of the CZ48 composite particles is slightly left-shifted, compared to the original CZ48 powders. FIG. 11 shows a comparison of DSC patterns between the CZ48 composite particles and the raw CZ48 particles. FIG. 11 shows the DSC difference between two particle forms. The DSC measurement showed that the melting point of the CZ48 composite particle material was about 80° C. lower than the original CZ48 powders, which is because the CZ48 composite particles contain excipients (F108, HPMC E3, and mannitol). Clearly, the CZ48 composite particles have different characters from the raw API (CZ48) powders. The CZ48 composite particles are 4 times smaller in size than the raw API, which should more easily absorbed by mans or animals.

Example 2

PK absorption of the CZ48 from CZ48 composite particles in mice and dogs was studied.

Figure 12A:
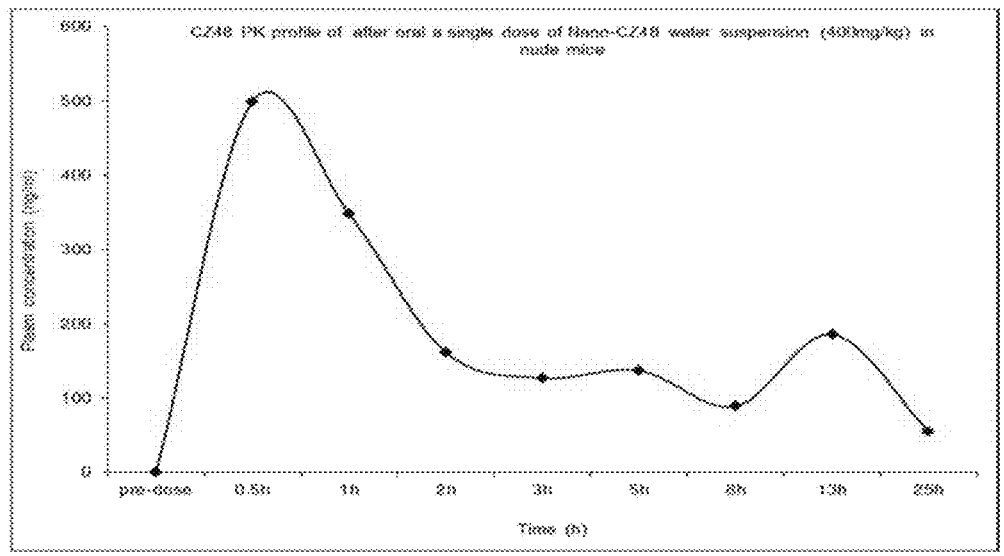
FIG. 12A shows a relationship between the concentration and time for the active ingredient CZ48 of CZ48 composite particles after a single dose administration according to an example of the present application.
Figure 12B:
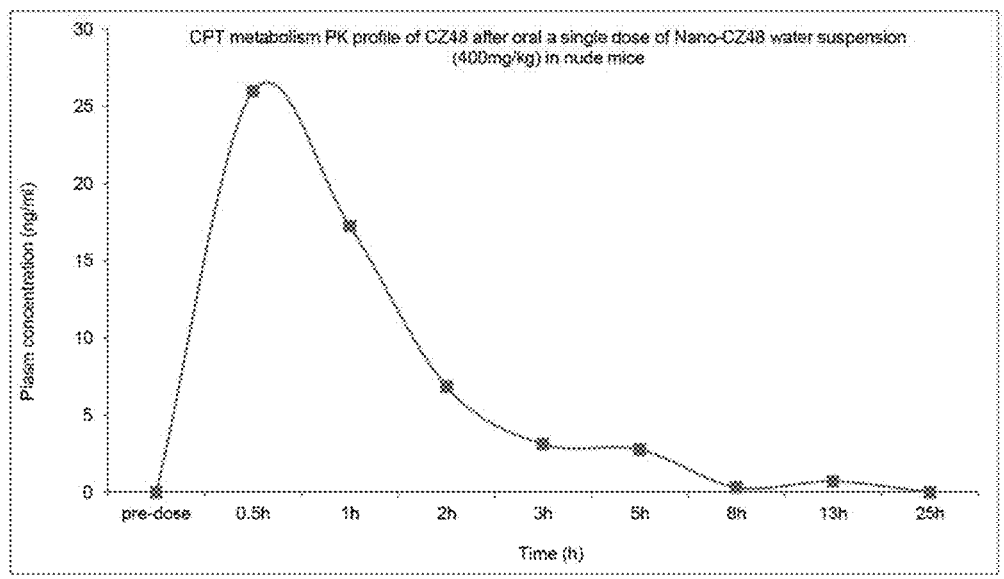
FIG. 12B shows a relationship between the concentration and time for the metabolite CPT of the active ingredient CZ48 of CZ48 composite particles after a single dose administration according to an example of the present application.

A group of 3 female healthy mice was administered with CZ48 composite particles equivalent to 400 mg/kg API. The blood samples were collected at time points of pre-dose, 0.5, 1, 2, 3, 5, 8, 13, and 25 h. After analysis by HPLC, concentration-time curves were obtained for the CZ48 composite particles and its metabolite CPT after a single dose administration as shown in FIGS. 12A-B. Selected parameters calculated from FIGS. 12A-B are listed in Table 3.

TABLE 3

PK parameters of CZ48 and its metabolite CPT.

CZ48 Source:
CZ48 Composite

| Particles | $C_{max}$ (ng/ml) | $T_{max}$ (h) | $AUC_{0-24}$ (ng · h · ml-1) |
|---|---|---|---|
| CZ48 | 499.4 | 0.5 | 3472.4 |
| CPT | 26.0 | 0.5 | 51.7 |

PK parameters of the CZ48 composite particles in mice were similarly determined for raw CZ48 powders for comparison, and PK parameters were similarly determined for both in dogs. The results are shown in Table 4. $C_{max}$ refers to the peak plasma concentration of the drug after administration. $T_{max}$ refers to time to reach $C_{max}$. AUC refers to the integral of the concentration-time curve.

TABLE 4

PK parameters of the CZ48 composite particles and raw CZ48 powders.

| Species | Formulation CZ48 Particles | Dose (mg/kg) (Based on API content) | $C_{max}$ | $T_{max}$ (h) | $AUC_{0-24}$ | AUC ratio (new: native) |
|---|---|---|---|---|---|---|
| Mouse | Composite | 400 | 499.4 | 0.5 | 3472.4 | 3.45:1 |
|  | Native | 400 | 89.4 | 1.0 | 1005.9 |  |
| Dog | Composite | 400 | 12.0 | 6 | 129.1 | 3.35:1 |
|  | Native | 400 | 3.4 | 4 | 38.7 |  |

The PK absorption of the CZ48 composite particles in mice and dog models was found to be 345% and 335%, respectively, higher than the original CZ48 powders.

Example 3

Biodistributions of the CZ48 composite particles in cancerous mice were studied.

Figure 13:
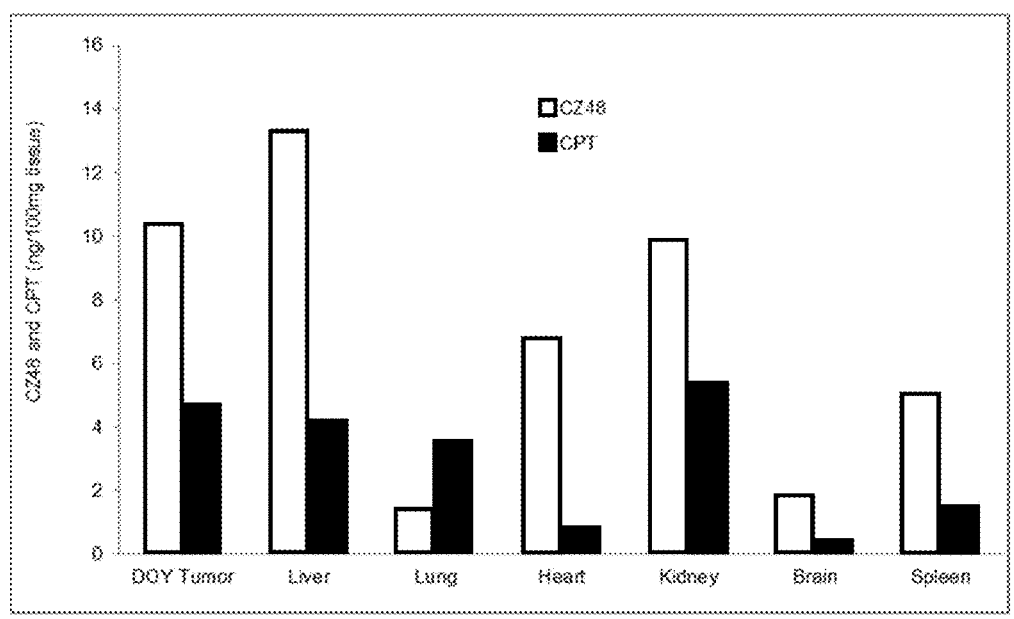
FIG. 13 shows biodistributions of CZ48 and CPT in tumor and other tissues of DOY mice according to an example of the present application.
Figure 14:
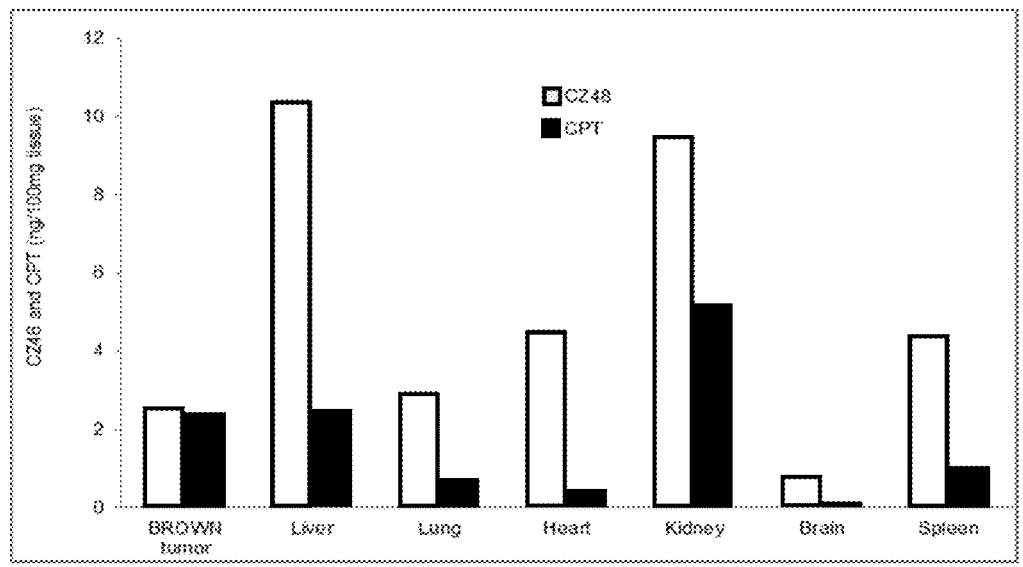
FIG. 14 shows biodistributions of CZ48 and CPT in tumor and other tissues of BRO mice according to an example of the present application.
Figure 15:
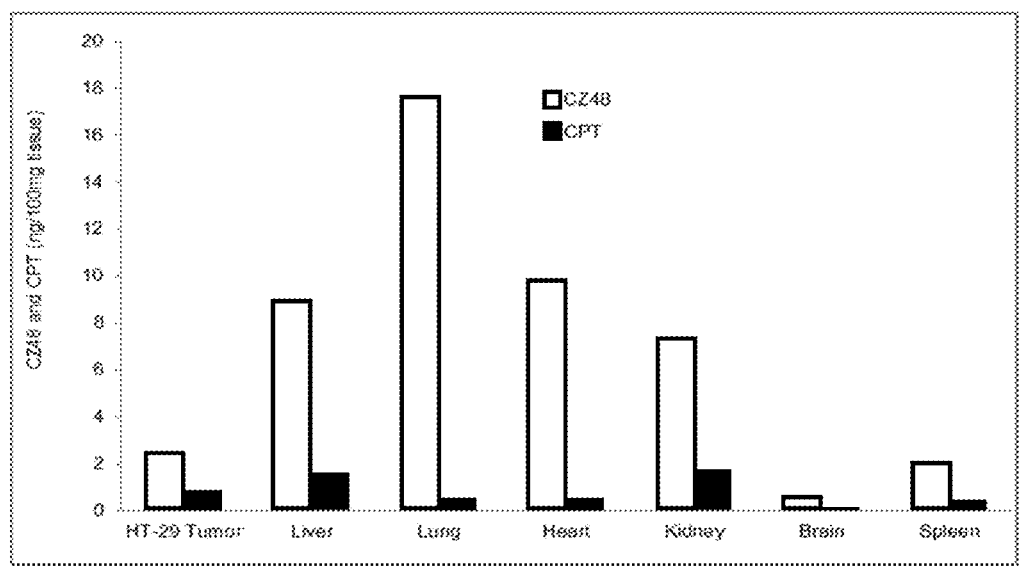
FIG. 15 shows biodistributions of CZ48 and CPT in tumor and other tissues of HT29 mice according to an example of the present application.

Three groups of mice, respectively carrying human DOY-lung, HT29-colon, and BRO-melanoma, were treated with CZ48 composite particles. At day 7 of the treatment, 3 DOY carrying mice were sacrificed and their tumor tissues and other major organ tissues, such as, liver, lung, heart, kidney, brain, and spleen were collected and processed. The CZ48 and its metabolite CPT concentrations in these tissues were measured by HPLC. The results are shown in FIG. 13. At day 52 of the treatment, 6 mice from HT29 and BRO groups (3 each group) were sacrificed and the same tissues as DOY group were collected and processed. After HPLC analysis, the drug distributions in tissues are shown in FIGS. 14 and 15.

Example 4

Anticancer activity of the CZ48 composite particles against human xenografts was studied in animal models.

Figure 16:
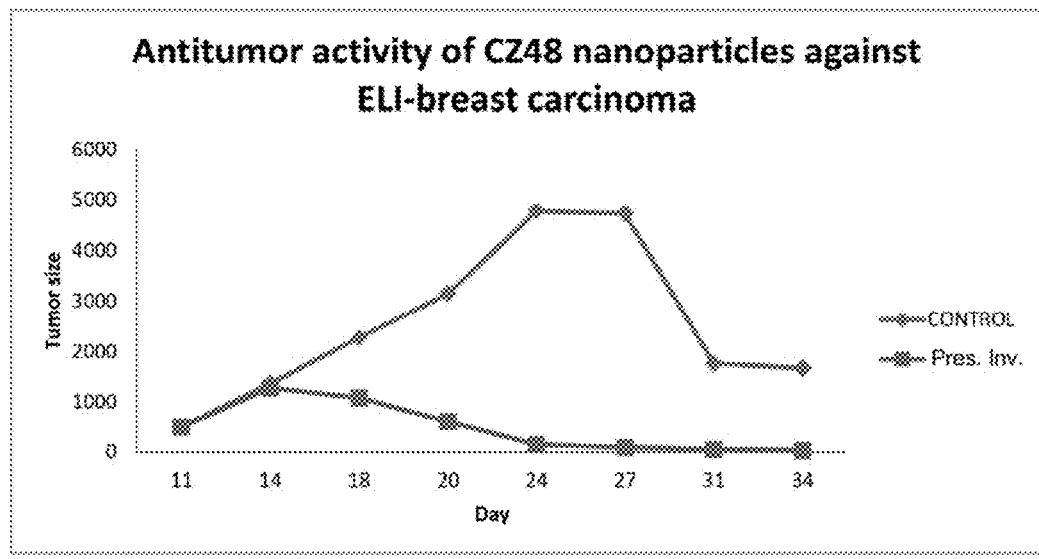
FIG. 16 shows the response of ELI-breast xenografts to the treatment with 100 mg/kg CZ48 composite particles according to an example of the present application.
Figure 17:
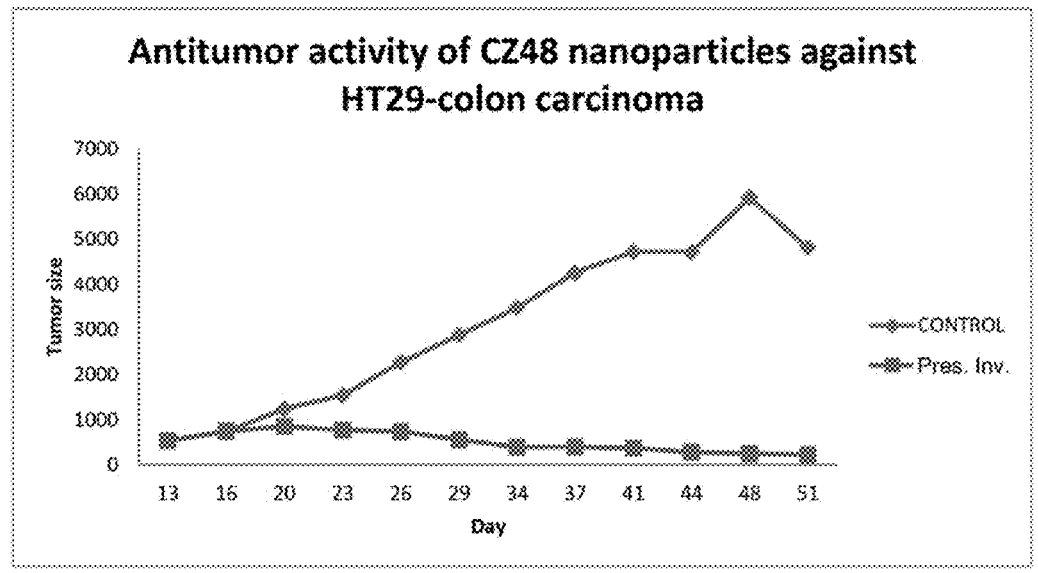
FIG. 17 shows the response of human HT29-colon tumor to the treatment with 200 mg/kg CZ48 composite particles according to an example of the present application.
Figure 18:
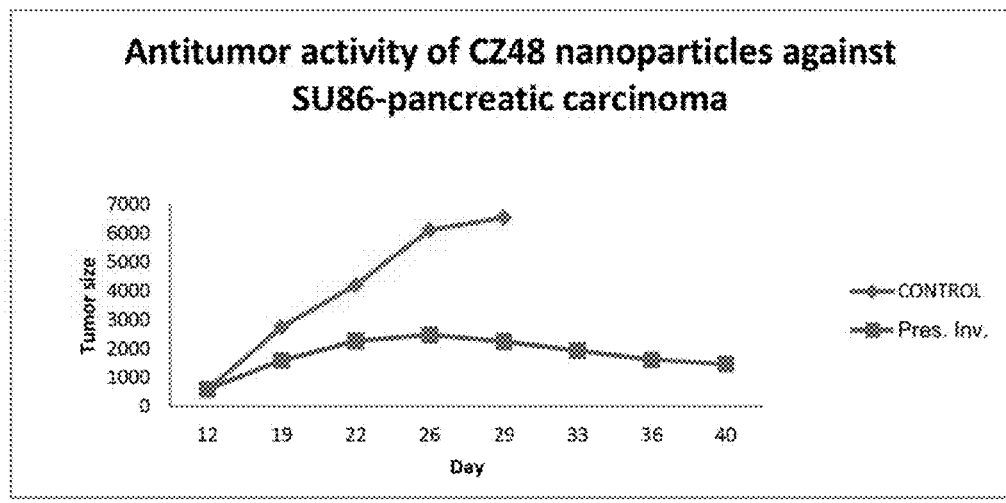
FIG. 18 shows the response of SU86-pancreatic tumor to the treatment with 125 mg/kg CZ48 composite particles according to an example of the present application.
Figure 19:
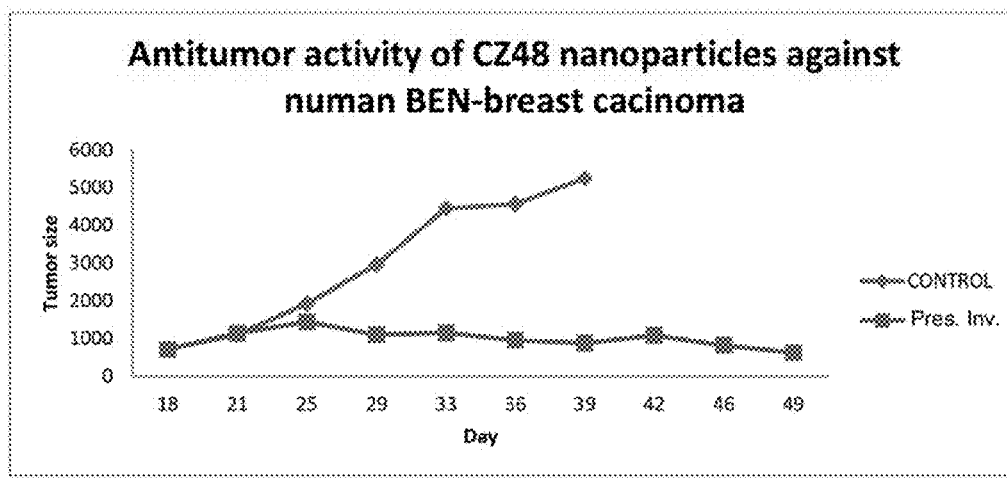
FIG. 19 shows the response of BEN-breast tumor to the treatment with 100 mg/kg CZ48 composite particles according to an example of the present application.

Four groups of nude mice were transplanted with 4 various human tumor xenografts, ELI-breast, HT29-colon, SU86-pancrea, and BEN-breast, in a manner of one group with one type of tumor. When tumors planted in mice started to grow exponentially, the treatment with the particles initialized and continued for a whole treating period. FIG. 16 shows the response of human ELI-breast tumor to the treatment with 100 mg/kg CZ48 composite particles. FIG. 17 shows the response of human HT29-colon tumor to the treatment with 200 mg/kg CZ48 composite particles. FIG. 18 shows the response of SU86-pancreatic tumor to 125 mg/kg matrix particles. The response of human BEN-breast tumor to the treatment with 100 mg/kg CZ48 composite particles material is shown in FIG. 19.

Table 5 summarizes the results of these 4 in vivo experiments.

TABLE 5

Anticancer activity and toxicity of the CZ48 composite particles in mice.

| Experiment | Activity against xenografts | | | Toxicity in mice |
|---|---|---|---|---|
| | Good | Slight | None | Survival/Total |
| SC1934: ELI-Breast (100 mg/kg) | X | | | 6/6 |
| SC1948: HT29-colon (200 mg/kg) | X | | | 5/5 |
| SC1958: 5U86-panc (125 mg/kg) | X- | | | 6/7 |
| 5C1968: BEN-breast (100 mg/kg) | X | | | 4/5 |

The CZ48 composite particles showed higher potency against human xenografts in nude mice than the native powders. For example, 200 mg/kg of the CZ48 composite particles showed good activity against HT29-colon tumor while the native API powders needed 1000 mg/kg to achieve the same result [Cao et al. Cancer Research 2009]. Thus, the CZ48 composite particles are a better formulation compared to the native API powders. As shown by these results, the CZ48 composite particle material were found to have good anticancer activity with minimal toxicity in mice as seen from the animal survival rate in each experiment The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A pharmaceutical composition comprising particles which are a physical mixture comprising at least one 20-camptothecin or a derivative thereof, at least one surfactant, at least one stabilizer, and at least one diluent, and the particles have a mean particle size of about 2500 nm or less.

2. The pharmaceutical composition of claim 1, wherein the particles having a mean particle size of from about 1600 nm to about 2000 nm.

3. The pharmaceutical composition of claim 1, wherein at least 90 vol. % of the particles have a particle size of about 2500 nm or less.

4. The pharmaceutical composition of claim 1, wherein the composition is a powder.

5. The pharmaceutical composition of claim 1, wherein the particles are discrete composite particles.

6. The pharmaceutical composition of claim 1, wherein particles have at least one of a Krumbein sphericity of at least about 0.5 and a roundness of at least about 0.4.

7. The pharmaceutical composition of claim 1, wherein the active pharmaceutical ingredient, the surfactant, the stabilizer, and the diluent each are in solid form.

8. The pharmaceutical composition of claim 1, wherein the 20-camptothecin or derivative thereof is at least one crystalline aliphatic ester of CPT in hydrated form having the formula

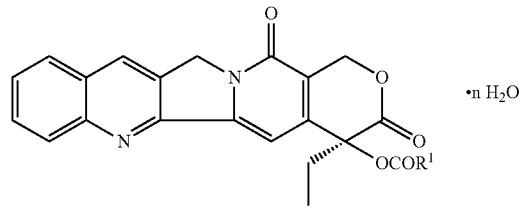

wherein n can represent any number ranging from 1 to 10, and $R^1$ represents a $C_2$-$C_6$ alkyl group.

9. The pharmaceutical composition of claim 1, wherein the 20-camptothecin or derivative thereof is at least one camptothecin ester having the formula:

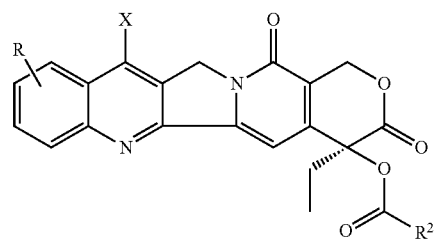

wherein R represents H, $NO_2$, $NH_2$, $N_3$, —OH, a halogen, carboxyl, a $C_{1-16}$ alkyl group, $C_{2-16}$ alkenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_nNR_2^7$ where $R^7$ can be H or a $C_{1-8}$ alkyl group and n can be an integer of from 1 to about 8, hydroxyl, SH, $SR^8$ where $R^8$ can be a $C_{1-8}$ alkyl group or an unsubstituted phenyl group or a substituted phenyl group, a carbonyl group $COR^9$ where $R^9$ can be a $C_{1-8}$ alkyl group or an unsubstituted phenyl group or a substituted phenyl group, or a $SiR_3^{10}$ where $R^{10}$ can be a $C_{1-4}$ alkyl group, and $R^2$ can be an alkyl group, a cycloalkyl group, an alkenyl group, or an epoxy group.

10. The pharmaceutical composition of claim 1, wherein the 20-camptothecin or derivative thereof is camptothecin-20-O-propionate hydrate.

11. The pharmaceutical composition of claim 1, wherein said surfactant is a poloxamer.

12. The pharmaceutical composition of claim 1, wherein said surfactant is a poly(ethylene oxide)-poly(propylene oxide)-poly(ethylene oxide) triblock copolymer wherein the poly(propylene oxide) block having an average molecular weight of from about 1500 to about 4500 Daltons and a poly(ethylene oxide) content of from about 50% to about 90% w/w of the copolymer.

13. The pharmaceutical composition of claim 1, wherein said stabilizer is at least one of a cellulose and a cellulose derivative.

14. The pharmaceutical composition of claim 1, wherein said stabilizer is methylcellulose, ethyl cellulose, hydroxyethyl cellulose, hydroxypropyl cellulose, hydroxypropyl methylcellulose, sodium carboxymethyl cellulose, cellulose acetate, cellulose actetate butyrate, cellulose phthalate, cellulose acetate phthalate, hydroxypropylmethylcellulose phthalate, or any combinations thereof.

15. The pharmaceutical composition of claim 1, wherein said diluent is mannitol, xylitol, lactitol, sorbitol, maltitol, cellobitol, erythritol, isomalt, lactose, potato starch, corn starch, glucose, sucrose, dextran, or any combinations thereof.

16. The pharmaceutical composition of claim 1, wherein said diluent is a sugar.

17. The pharmaceutical composition of claim 1, wherein said diluent is mannitol.

18. The pharmaceutical composition of claim 1, wherein the mixture comprises from about 1 wt % to about 90 wt % 20-camptothecin or a derivative thereof, from about 1 wt % to about 20 wt % surfactant, from about 1 wt % to about 20 wt % stabilizer, and from about 5 wt % to about 95 wt % diluent, based on total weight of the mixture.

19. The pharmaceutical composition of claim 1, wherein the mixture comprises from about 10 wt % to about 80 wt % camptothecin-20-O-propionate hydrate, from about 1 wt % to about 10 wt % surfactant, from about 1 wt % to about 10 wt % stabilizer, and from about 10 wt % to about 90 wt % diluent, based on total weight of the mixture.

20. The pharmaceutical composition of claim 1, wherein the mixture comprises from about 25 wt % to about 50 wt % camptothecin-20-O-propionate hydrate, from about 1 wt % to about 10 wt % poloxamer surfactant, from about 1 wt % to about 10 wt % cellulose-based stabilizer, and from about 40 wt % to about 80 wt % sugar diluent, based on total weight of the mixture.

21. A pharmaceutical composition of claim 1, wherein the composition is suitable for oral administration.

22. An oral pharmaceutical suspension comprising the pharmaceutical composition of claim 1 suspended in carrier fluid.

23. An oral pharmaceutical suspension comprising the pharmaceutical composition of claim 1 suspended in water.

24. A capsule containing the pharmaceutical composition of claim 1.

25. A capsule containing the pharmaceutical composition of claim 1 in loose dry powder form.

26. A caplet comprising a tablet containing the pharmaceutical composition of claim 1, wherein the tablet is coated with a protective coating.

* * * * *